(12) United States Patent
Zang et al.

(10) Patent No.: US 12,221,489 B2
(45) Date of Patent: *Feb. 11, 2025

(54) ANTIBODIES TO HUMAN B7x FOR TREATMENT OF METASTATIC CANCER

(71) Applicants: ALBERT EINSTEIN COLLEGE OF MEDICINE, Bronx, NY (US); SLOAN-KETTERING INSTITUTE FOR CANCER RESEARCH, New York, NY (US)

(72) Inventors: Xingxing Zang, New York, NY (US); James P. Allison, Houston, TX (US)

(73) Assignees: ALBERT EINSTEIN COLLEGE OF MEDICINE, Bronx, NY (US); SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 692 days.

This patent is subject to a terminal disclaimer.

(21) Appl. No.: 17/004,331

(22) Filed: Aug. 27, 2020

(65) Prior Publication Data

US 2020/0392246 A1   Dec. 17, 2020

Related U.S. Application Data

(60) Continuation of application No. 15/252,267, filed on Aug. 31, 2016, now abandoned, which is a division of application No. 14/050,512, filed on Oct. 10, 2013, now Pat. No. 9,447,186, which is a continuation-in-part of application No. PCT/US2012/034348, filed on Apr. 20, 2012.

(60) Provisional application No. 61/477,729, filed on Apr. 21, 2011.

(51) Int. Cl.
| | |
|---|---|
| C07K 16/28 | (2006.01) |
| A61K 9/00 | (2006.01) |
| A61K 39/395 | (2006.01) |
| A61K 45/06 | (2006.01) |
| A61K 49/00 | (2006.01) |
| C07K 16/30 | (2006.01) |
| G01N 33/50 | (2006.01) |
| A61K 39/00 | (2006.01) |

(52) U.S. Cl.
CPC ............ *C07K 16/30* (2013.01); *A61K 9/0019* (2013.01); *A61K 39/3955* (2013.01); *A61K 39/39558* (2013.01); *A61K 45/06* (2013.01); *A61K 49/0008* (2013.01); *C07K 16/28* (2013.01); *C07K 16/2827* (2013.01); *C07K 16/3015* (2013.01); *C07K 16/3023* (2013.01); *C07K 16/303* (2013.01); *C07K 16/3038* (2013.01); *C07K 16/3046* (2013.01); *C07K 16/3053* (2013.01); *C07K 16/3069* (2013.01); *G01N 33/5011* (2013.01); *A61K 2039/505* (2013.01); *C07K 2317/34* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,891,030 B2 | 5/2005 | Chen |
| 6,962,980 B2 | 11/2005 | Mitcham et al. |
| 7,888,477 B2 | 2/2011 | Bangur et al. |
| 9,447,186 B2 | 9/2016 | Zang et al. |
| 10,689,432 B2 | 6/2020 | Zang et al. |
| 2004/0175380 A1 | 9/2004 | Allison et al. |
| 2005/0163772 A1 | 7/2005 | Dong |
| 2008/0138805 A1 | 6/2008 | Condeelis |
| 2008/0206235 A1 | 8/2008 | Lieping |
| 2009/0074650 A1 | 3/2009 | Korman et al. |
| 2009/0074660 A1 | 3/2009 | Korman et al. |
| 2009/0136490 A1 | 4/2009 | Pilkington et al. |
| 2009/0208489 A1 | 8/2009 | Veiby et al. |
| 2009/0215084 A1 | 8/2009 | Kwon et al. |
| 2010/0048478 A1 | 2/2010 | Tykocinski et al. |
| 2010/0136009 A1 | 6/2010 | Papkoff et al. |
| 2010/0203056 A1 | 8/2010 | Irving et al. |
| 2011/0059470 A1 | 3/2011 | Condeelis et al. |
| 2011/0085970 A1 | 4/2011 | Terrett et al. |
| 2012/0207759 A1 | 8/2012 | Murphy et al. |
| 2012/0276095 A1 | 11/2012 | Langermann et al. |
| 2014/0294861 A1 | 10/2014 | Scholler et al. |
| 2014/0322129 A1 | 10/2014 | Leong |
| 2014/0356364 A1 | 12/2014 | Langermann et al. |
| 2015/0315275 A1 | 11/2015 | Langermann |

FOREIGN PATENT DOCUMENTS

WO    2009073533 A2    6/2009

OTHER PUBLICATIONS

International Search Report and Written Opinion for International Application No. PCT/US2014/069191 issued Mar. 9, 2015; 9 pages.
Mallat et al. "The role of adaptive T cell immunity in atherosclerosis" J. Lipid Res. 2009, vol. 50; S364-S369.

(Continued)

*Primary Examiner* — Ilia I Ouspenski
(74) *Attorney, Agent, or Firm* — Perkins Coie LLP

(57) ABSTRACT

Methods are provided for treating metastatic cancer in patients having metastatic cancer or for preventing metastasis in cancer patients at risk for metastasis comprising administering to the patient an antibody to B7x, or an active antibody fragment that binds B7x, in an amount effective to treat or prevent metastasis.

13 Claims, 18 Drawing Sheets
Specification includes a Sequence Listing.

(56) References Cited

OTHER PUBLICATIONS

Yamaura K et al. "In Vivo Function of Immune Inhibiry Molecule B7-H4 in Alloimmune Responses" American Journal of Transplantation, 2010, vol. 10, pp. 2355-2362.
Zeng et al. "BTLA, a New Inhibitory B7 Family Receptor with a TNFR Family Ligand" Cellular & Molecular Immunology, 2005, vol. 2, No. 6, pp. 427-432.
ISA, International Search Report, dated Jul. 6, 2012 in connection with PCT International Application No. PCT/US2012/034348, 5 pages.
ISA, Written Opinion of the International Searching Authority, dated Jul. 6, 2012 in connection with PCT International Application No. PCT/US2012/034348, 4 pages.
Abadi Y M et al., entitled "Host b7x promotes pulmonary metastasis of breast cancer," J Immunol, Apr. 1, 2013 ;190 (7):3806-14, Abstract Only, Epub Mar. 1, 2013.
Abdiche et al. mAbs (2016) 8: 264-277.
Boyd et al. Current Opinion in Immunology 2016, 40: 103-109.
Conroy et al. Methods (2017) 116: 12-22.
Dangaj et al., (2013), Cancer Res; 73(15): 4820-4829.
Ferrara et al. mAbs (2015) 7: 32-41.
Jeon H, et al., entitled "B7x and myeloid-dervied suppressor cells in the tumor microenvironment," OncoImmunology 2:7, e24744-1-e24744-3; Jul. 2013.
Jeon H. et al. Cell Reports, 2014, vol. 9, pp. 1089-10698.
Khan et al. Sci. Rep. (2017) 7, 45163; doi: 10.1038/srep45163 (12 pages).
Konitzer et al. mAbs (2017) 9: 536-549.
Lee et al. Nature Medicine (2016) 22: 1456-1464.
NCBI Entry NP _078902.2, accessed on Jul. 2, 2015, 3 pages.
Parola et al. Immunology (2018) 153: 31-41.
Prasad et al., (2013) Immunity, vol. 18, 863-873.
Sheehan et al. Microbial. Spectr. (2015) 3(1): AID-0028-2014; 17 pages.
Sica et al., (2013) Immunity, vol. 18, 849-861.
Thompson RH et al., entitled "Serum-Soluble B7x Is Elevated in Renal Cell Carcinoma Patients and Is Associated with Advanced Stage," Cancer Res 2008; 68: (15), Aug. 1, 2008, 6054-6058.
Van Regenmortel MHV. Front. Immunol. (2018) vol. 8, Article 2009 (11 pages).
Zang H et al., entitled "B7-H3 and B7x are highly expressed in human prostate cancer and associated with disease spread and poor outcome," PNAS, vol. 104, No. 49, Dec. 4, 2007, 19458-19463.
Zang H et al., entitled "B7x: A widely expressed B7 family member that inhibits T cell activation," PNAS, vol. 100, No. 18, Sep. 2, 2003, 10398-10392.
Zang H et al., entitled Tumor associated endothelial expression of B7-H3 predicts survival in ovarian carcinomas, Modern Pathology, 2010, 23, 1104-1112.
Zang X et al., entitled "The B7 Family and Cancer Therapy: Costimulation and Coinhibition," Clin Cancer Res 2007;13 (18) Sep. 15, 2007, 5271-5279.
Zhou et al. Cell (2015) 161: 1280-1292.

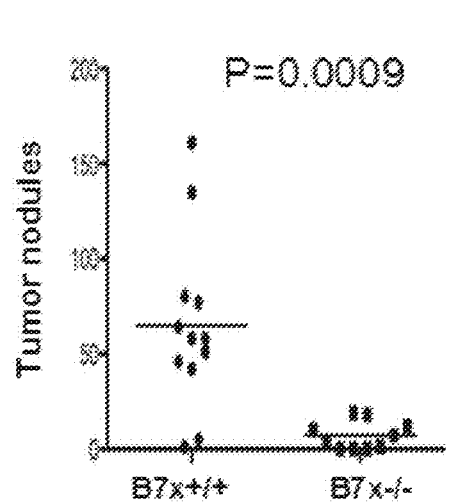
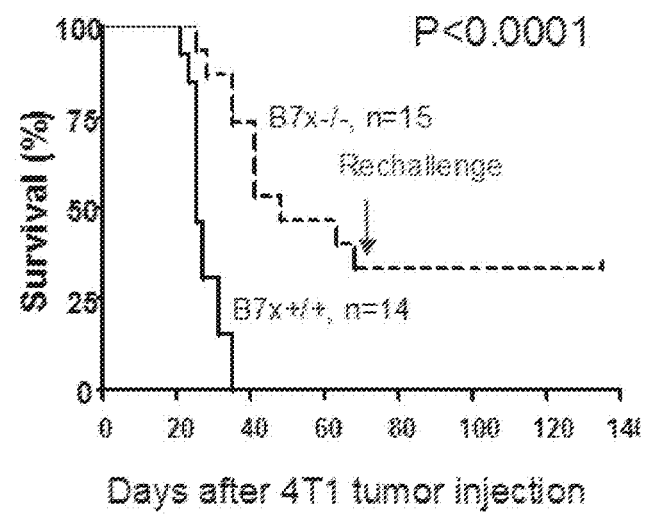
Fig. 4A              Fig. 4B
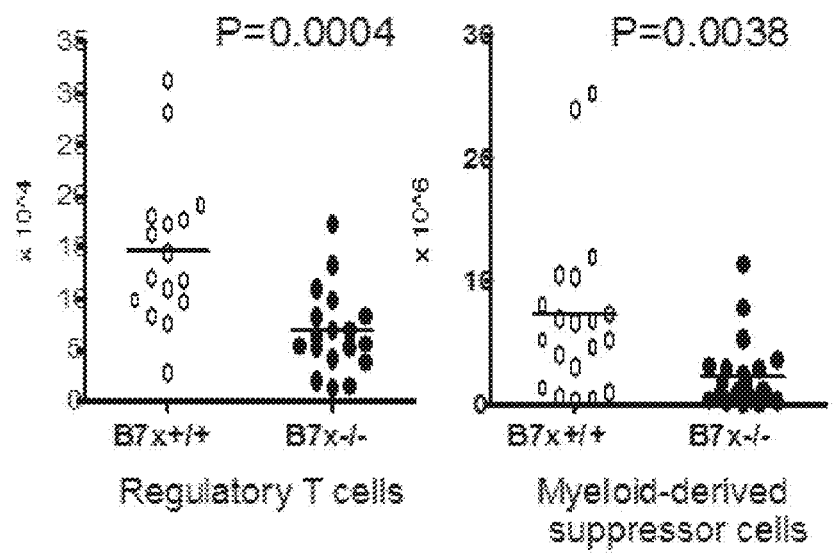
Fig. 4C

ANTIBODIES TO HUMAN B7x FOR TREATMENT OF METASTATIC CANCER

CROSS-REFERENCE TO RELATED APPLICATIONS

This application is a continuation of U.S. patent application Ser. No. 15/252,267, filed Aug. 31, 2016, which is a divisional of U.S. patent application Ser. No. 14/050,512, filed Oct. 10, 2013, now U.S. Pat. No. 9,447,186, which is continuation-in-part of and claims priority of PCT International Patent Application No. PCT/US2012/034348, filed Apr. 20, 2012, which designates the United States of America and which claims the benefit of U.S. Provisional Patent Application No. 61/477,729, filed Apr. 21, 2011, the contents of which are herein incorporated by reference in their entirety.

STATEMENT OF GOVERNMENT SUPPORT

This invention was made with government support under grant number DK083076 awarded by the National Institutes of Health and grant number W81XWH-10-1-0318 awarded by the United States Army Medical Research and Materiel Command. The government has certain rights in the invention.

BACKGROUND OF THE INVENTION

Throughout this application various publications are referred to in superscripts. Full citations for these references may be found at the end of the specification. The disclosures of these publications are hereby incorporated by reference in their entirety into the subject application to more fully describe the art to which the subject invention pertains.

Cancer is a serious public health problem in the U.S. and other countries. More than 90% of cancer patient deaths result from cancer metastasis rather than from a primary cancer. There are about 924,310 new cancer cases and 339,150 cancer deaths in the U.S. alone. According to Cancer Statistics 2010, in the U.S. in 2010 alone, there are an estimated 222,520 new cases and 157,300 deaths for lung cancer, 217,730 new cases and 32,050 deaths for prostate cancer, 207,090 new cases and 39,840 deaths for breast cancer, 145,500 new cases and 51,370 deaths for gut cancer, 58,240 new cases and 8,210 deaths for kidney cancer, and 51,350 new cases and 36,800 deaths for pancreas cancer. While traditional therapies such as surgery, chemotherapy, and radiation can often control primary cancer growth, successful control of disseminated metastases of cancer remains rare.

Cancer and the immune system have dynamic interactions, which play crucial roles in determining tumor development and thus clinical outcome. T cells of the immune system are the major combatants against cancers. T cell activation, proliferation, differentiation to effector function and memory generation are determined by both positive costimulation and negative coinhibition, generated mainly by the interaction between the B7 family and their receptor CD28 family (FIG. 1). In 2003, B7x was discovered as a new member of the B7/CD28 family[1]. B7x inhibits T cell function in vitro[1]. B7x is extremely conservative with 87% amino acid identity between human and mice.

A study of 823 prostatectomy patients for whom a minimum of 7 year follow-up data were available revealed that prostate cancer patients with strong expression of B7x by tumor cells were significantly more likely to have disease spread at time of surgery, and were at significantly increased risk of clinical cancer recurrence and cancer-specific death[2]. In addition, all of 103 ovarian borderline tumors tested expressed B7x[3]. In contrast, only scattered B7x-positive cells were detected in non-neoplastic ovarian tissues. Other investigators have reported that B7x is over-expressed in human cancers of the lung[4], ovary[5], breast[6,7], kidney[8], brain[9], pancreas[10], esophagus[17], skin[18], gut[36], stomach[19] and thyroid[35]. In renal cell carcinoma, patients with tumors expressing B7x were three times more likely to die from renal cancer compared to patients lacking B7x[8]. In human breast cancer, there was a significant association between a high proportion of B7x positive cells in invasive ductal carcinomas and decreased number of tumor infiltrating lymphocytes. In esophageal squamous cell carcinoma, expression levels of B7x on tumor cells were significantly correlated with distant metastasis, tumor stage and poor survival, and were inversely correlated with densities of CD3+ T cells in tumor nest and CD8+ T cells in tumor stroma.

The present invention addresses the serious and long-felt need for treatments for metastatic cancer.

SUMMARY OF THE INVENTION

Methods are provided for treating metastatic cancer in a patient having metastatic cancer or for preventing metastasis in a cancer patient at risk for metastasis comprising administering to the patient an antibody to B7x, or an active antibody fragment that binds B7x, in an amount effective to treat or prevent metastasis.

Methods are also provided for treating metastatic cancer in a patient having metastatic cancer or for preventing metastasis in a cancer patient at risk for metastasis comprising determining the level of B7x expression in a tumor sample from the patient, and if B7x is over-expressed in the tumor sample compared to healthy tissue, administering to the patient an antibody to B7x, or an active antibody fragment that binds B7x, in an amount effective to treat or prevent metastasis.

Methods are also provided for producing a monoclonal antibody to B7x comprising immunizing a B7x knockout mouse with a B7x-Ig fusion protein, generating a hybridoma from spleen cells from the mouse, and testing supernatant from the hybridoma for its ability to react with immobilized B7x-Ig or a cell line expressing B7x, but not with control Igs or cell lines expressing other B7 family members, to identify a monoclonal antibody to B7x.

Methods are further provided for screening monoclonal antibodies to B7x to identify an antibody that inhibits tumor growth in vivo comprising injecting tumor cells expressing B7x on their cell surface into a mouse to induce a tumor in the mouse, and injecting a monclonal antibody to B7x into the mouse to identify an antibody that inhibits tumor growth in vivo.

Methods are in addition provided for preventing reoccurrence of a tumor in a patient comprising administering to the patient an antibody to B7x, or an active antibody fragment that binds B7x, in an amount effective to prevent reoccurrence of a tumor in a patient.

group II consists of the pathway of PD-L1/PD-L2/PD-1; and group III contains B7-H3 and B7x, whose receptors are currently unknown. Modified from Zang et al.[1]

Figure 1:
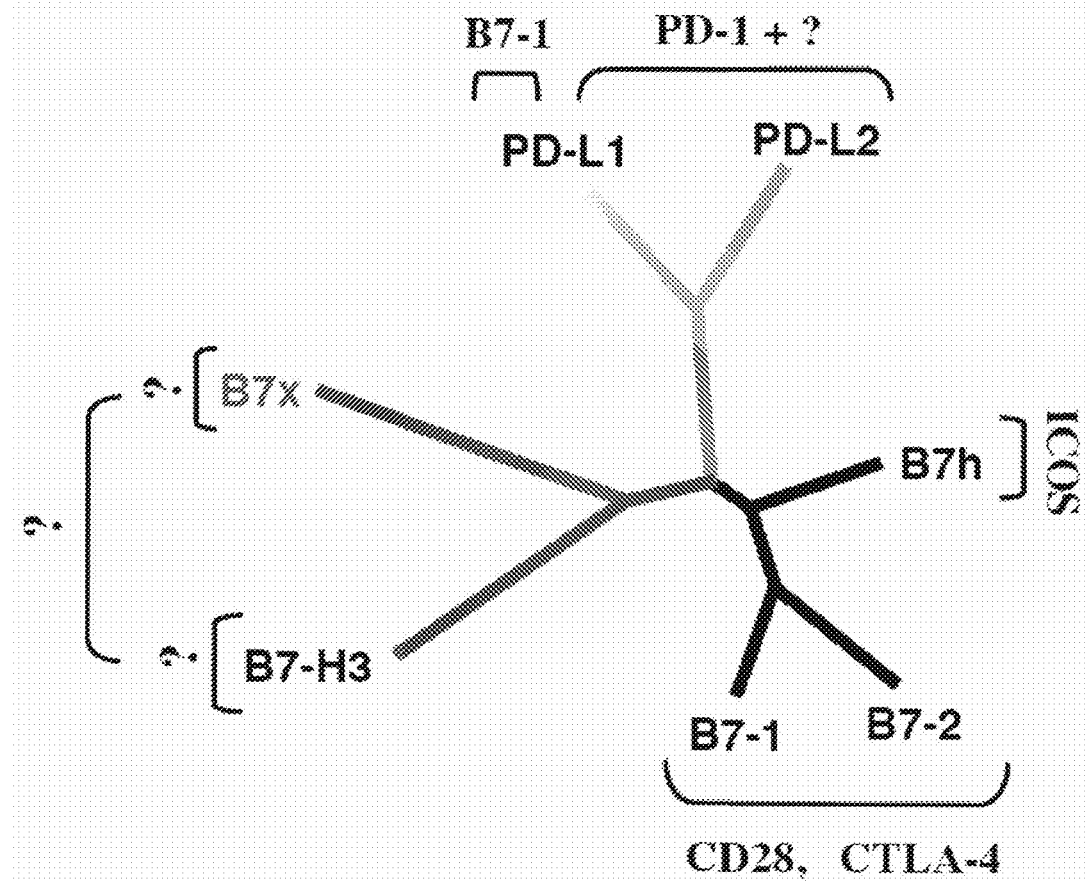
FIG. 1. The B7 family/CD28 family. The members of the B7 and CD28 families have been divided into three groups by phylogenetic analysis: group I includes the pathway of B7-1/B7-2/CD28/CTLA-4, and the pathway of B7h/ICOS.
Figure 2A:
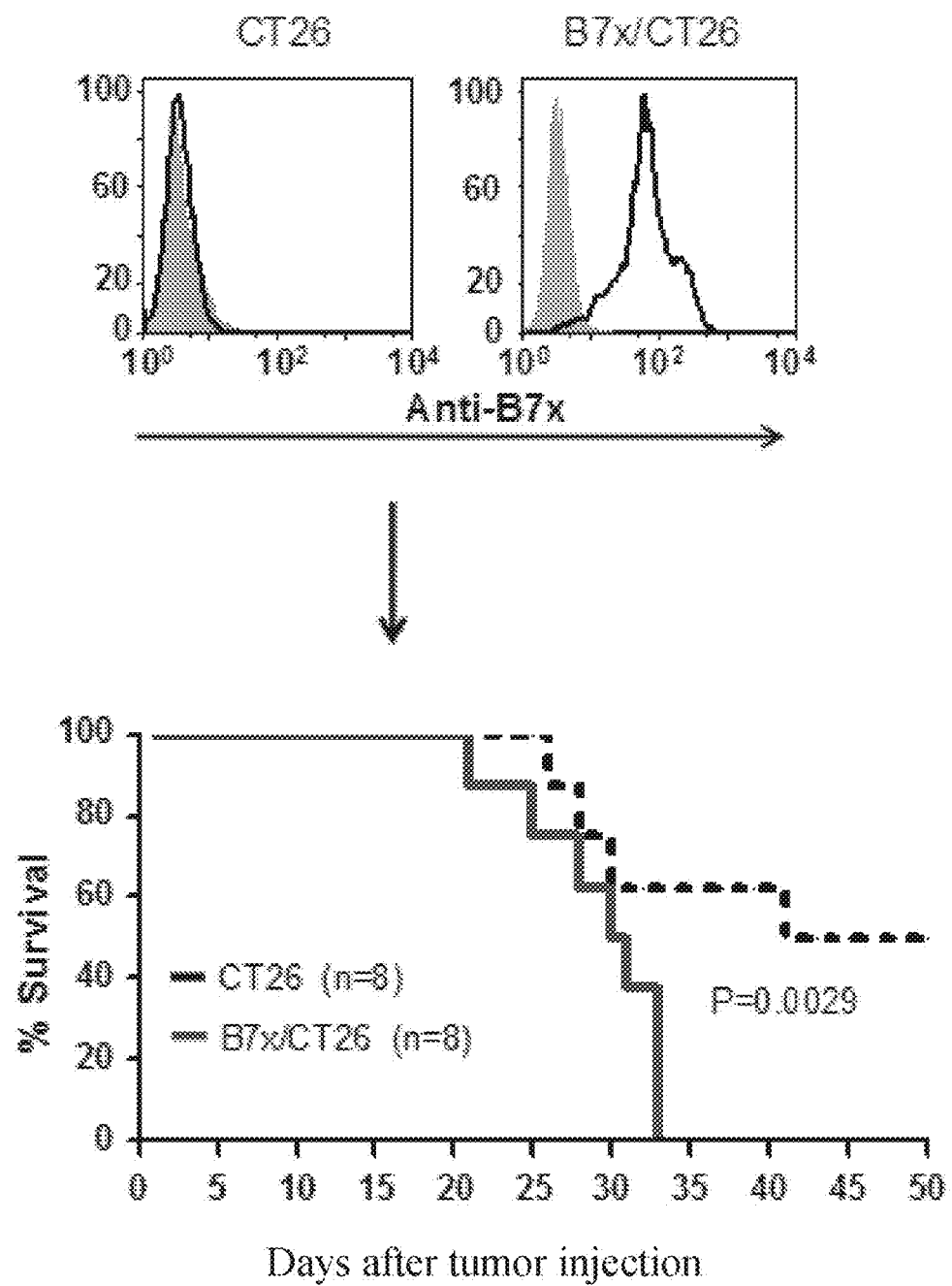
Figure 2B:
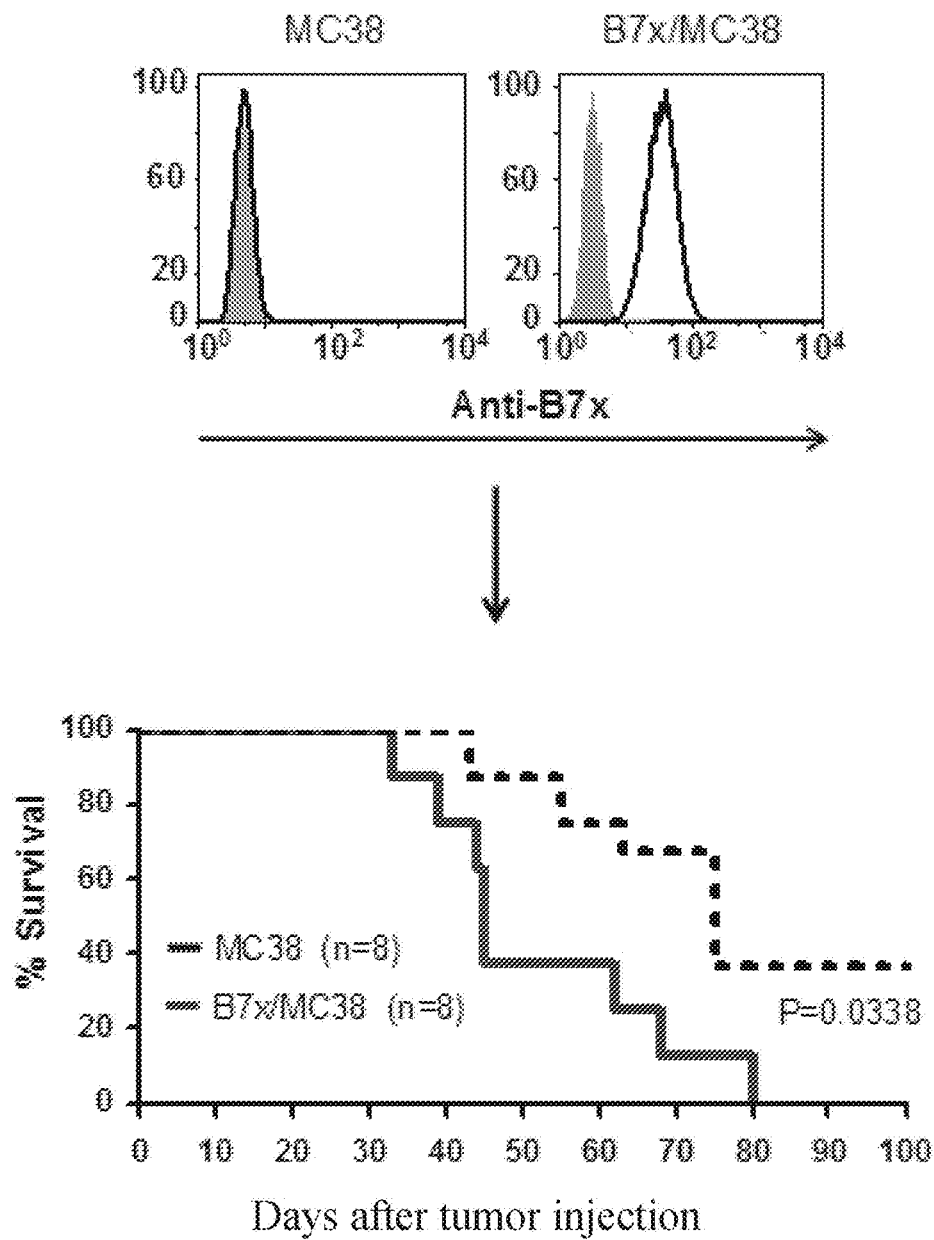

FIG. 2A-2B. Expression of B7x on tumor CT26 (A) or MC38 (B) accelerates disease progression in vivo. FACS analysis with PE-anti-B7x (line) or control PE-Ab (solid) showed that tumor cell lines CT26 and MC38 did not express B7x and that transfectants B7x/CT26 and B7x/MC38 expressed abundant cell surface B7x. Survival curves showed that syngeneic mice iv injected with B7x/CT26 or B7x/MC38 died much faster than mice injected with CT26 or MC38. The log-rank test was used for statistical analyses. P-values<0.05 were considered statistically significant.

Figure 3:
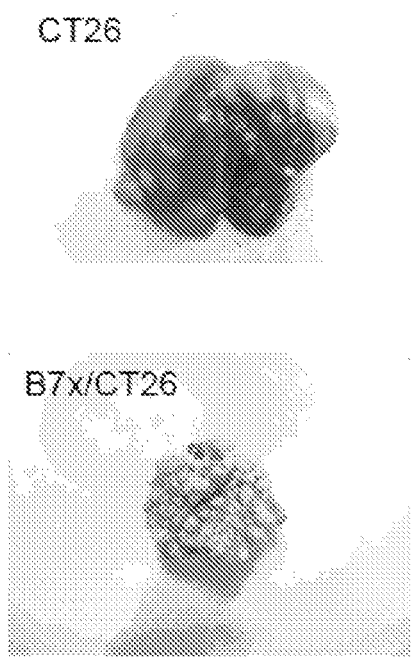
Figure 3:
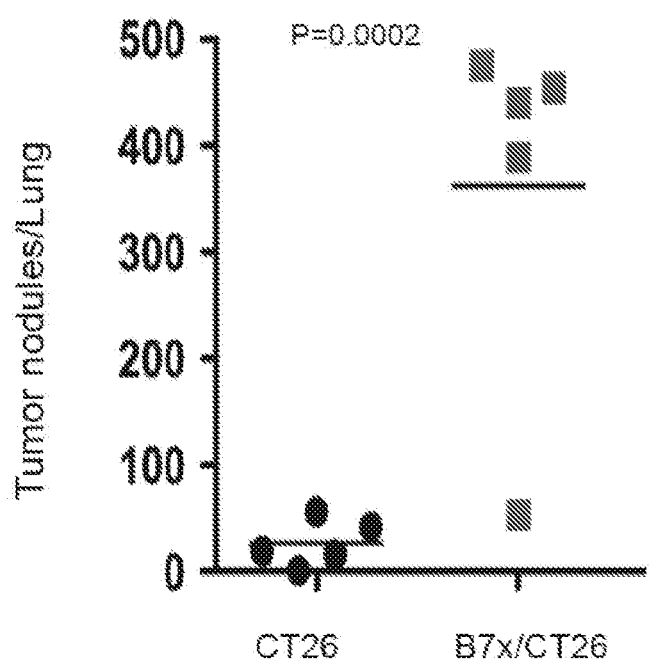

FIG. 3. Syngeneic BLAB/c mice iv injected with CT26 or B7x/CT26 and killed on day 20 for determining tumor nodules in lungs. Mice receiving B7x/CT26 had more tumor nodules than mice receiving CT26, P=0.0002.

FIG. 4A-4C. B7x deficiency protects mice from lung metastasis of cancer. After intravenous injection with breast cancer cell line 4T1, B7x knock-out (B7x-/-) mice had fewer tumor nodules than Balb/c wildtype (B7x+/+) mice at day 18 (A); all wildtype mice were dead within 36 days whereas 33% of B7x-/- mice were still alive at day 72 (B). Surviving B7x-/- mice were still alive at day 140 after rechallenge with 4T1(B), and no tumor was found in lungs from surviving B7x-/- mice with 4T1 double-challenge. Wildtype mice had more regulatory T cells and myeloid-derived suppressor cells in lungs than B7x-/- mice during lung metastasis of cancer (C).

Figure 5:
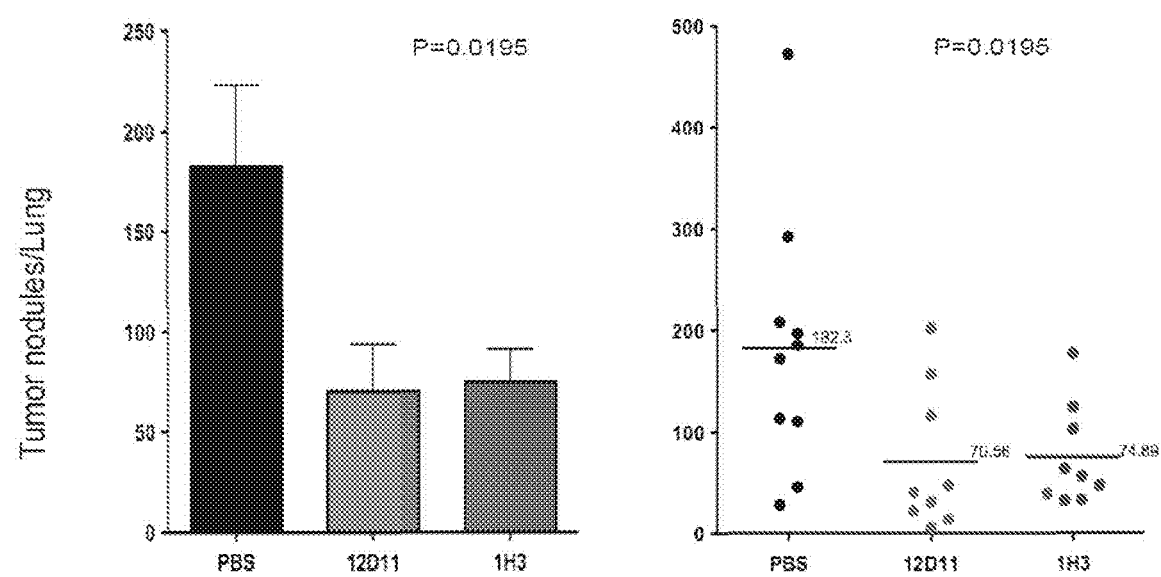

FIG. 5. Monoclonal antibody clones 12D11 and 1H3 reduced more than 50% tumor nodules in a lung metastasis of cancer model.

Figure 6:
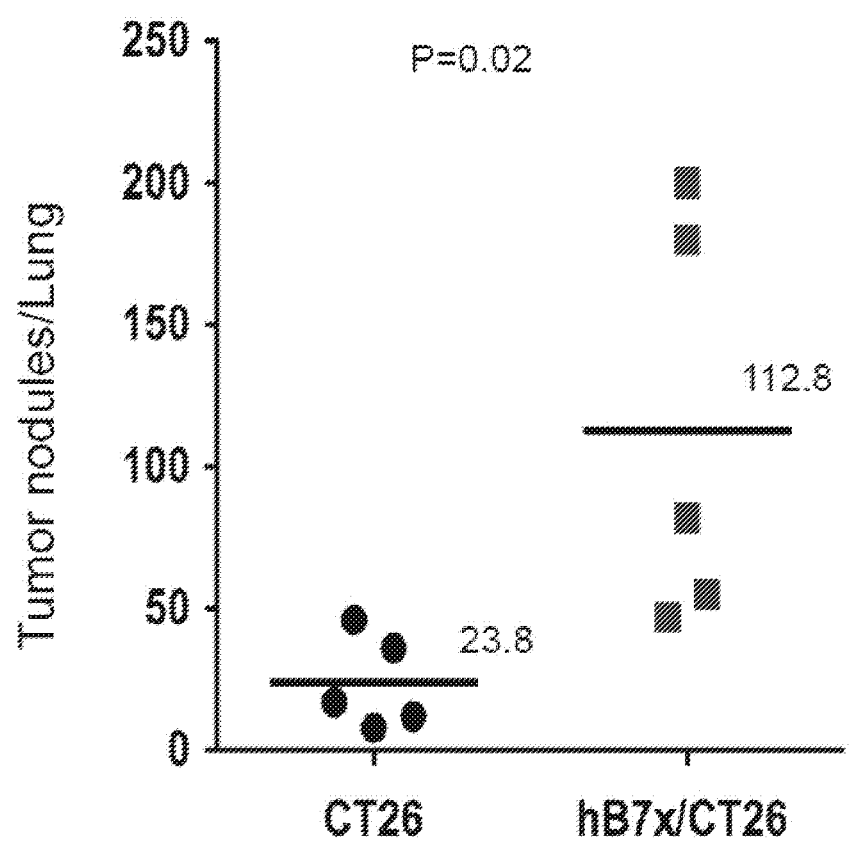

FIG. 6. BLAB/c mice iv injected with CT26 or hB7x/CT26 and killed on day 17 for determining tumor nodules in lungs. Mice receiving hB7x/CT26 had more tumor nodules than mice receiving CT26, P=0.02.

Figure 7:
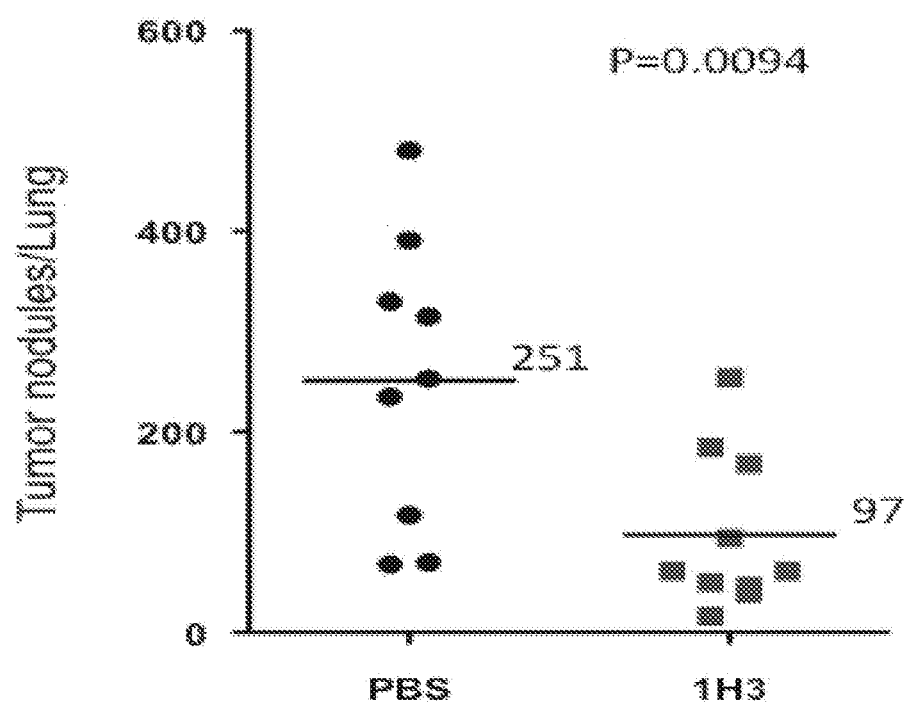

FIG. 7. Anti-B7x monoclonal antibody 1H3 reduced more than 60% of tumor nodules in a human B7x-expressed lung metastasis of cancer model.

Figure 8:
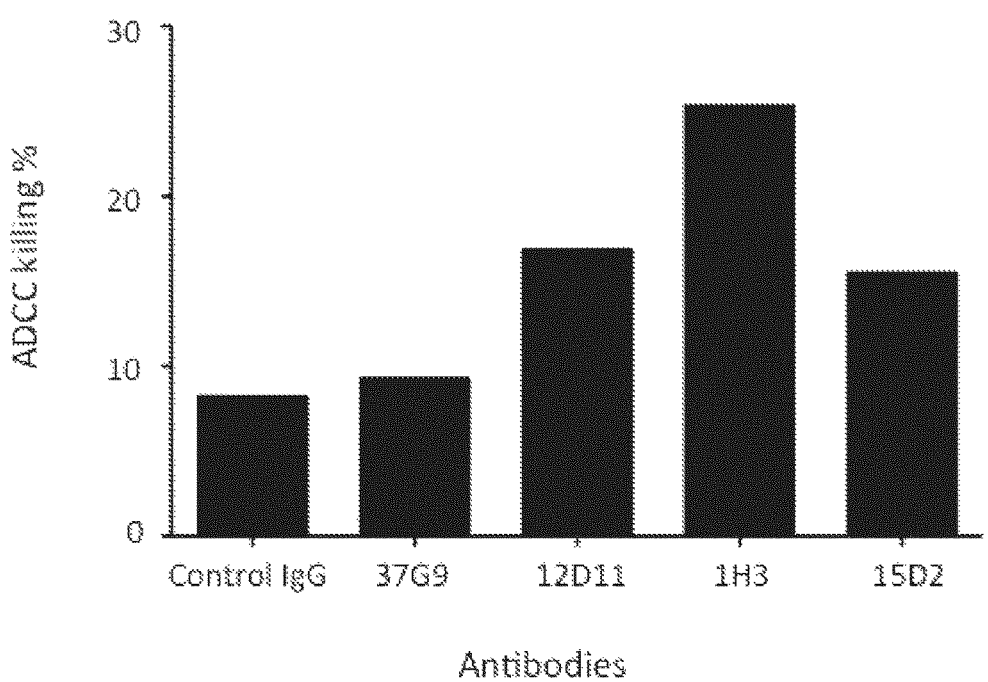

FIG. 8. Antibody-dependent cell-mediated cytotoxicity (ADCC) assay showed that three mAbs (1H3, 12D11, 15D2), but not 37G9, were able to kill tumor cells by ADCC mechanism.

Figure 9:
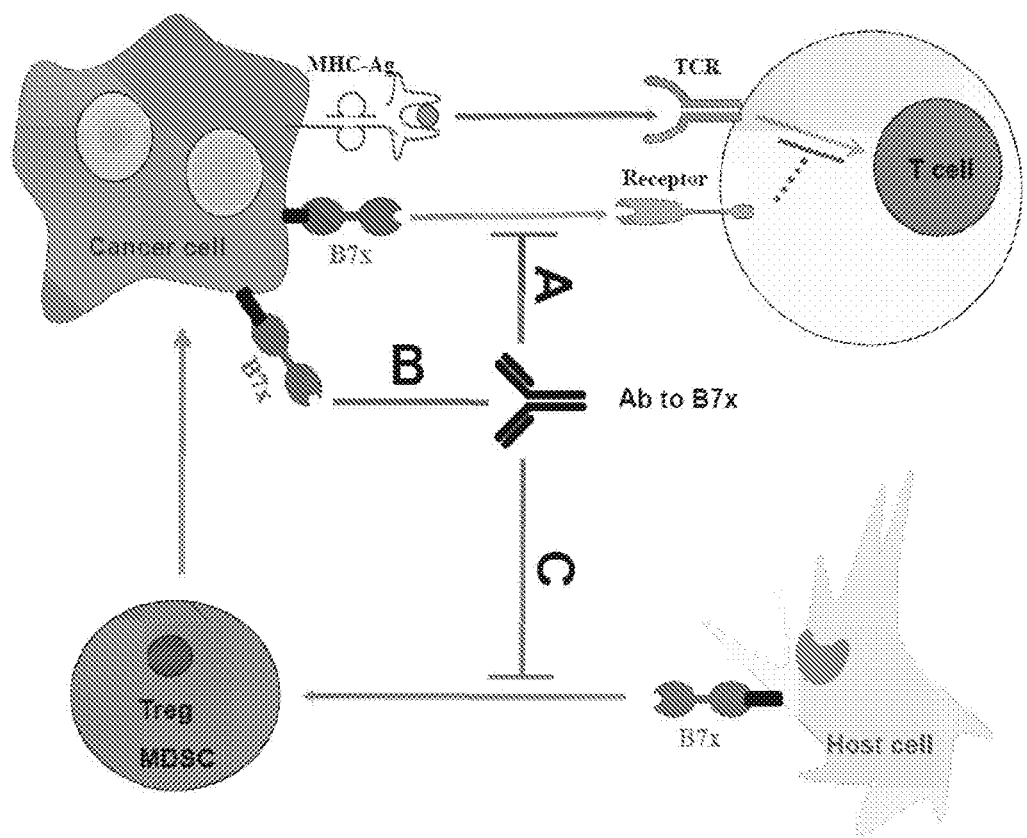

FIG. 9. Possible mechanisms by which treatment with anti-B7x antibodies inhibit metastatic cancer progression in vivo (see Experimental Details for discussion).

FIG. 10A-10D. The effect of anti-B7x monoclonal antibodies on tumor growth and survival of mice. (A) BALB/c mice were iv injected with CT26 cells expressing mouse B7x (B7x/CT26) at day 0 and then with anti-B7x mAbs 12D11 and 1H3 or control mouse IgG. After sacrifice, tumor nodules in lungs were counted. Data were pooled from three independent experiments (n=9 or 10). (B) BALB/c females were injected with 4T1 cells expressing mouse B7x (B7x/4T1) in the mammary fatpad. Mice were ip treated with mAb 1H3. After mice were sacrificed, breast tumors induced tumor nodules on lungs were counted (n=10). (C) BALB/c mice were iv injected with CT26 cells expressing human B7x (hB7x/CT26) at day 0 and then injected ip with mAb 1H3 or control mouse IgG. After mice sacrifice, tumor nodules in lungs were counted (n=9). Results were pooled from two independent experiments. (D) BALB/c mice were iv injected with B7x/CT26 at day 0 and then injected ip with 1H3 or control mouse IgG. At day 60 post-injection, remaining mice were iv re-challenged with B7x/CT26 (n=10).

FIG. 11A-11G. Anti-B7x therapy alters the intratumor balance of anti-tumor effector immune cells and immunosuppressive cells. BALB/c mice were iv injected with B7x/CT26 and then treated with 1H3 or control mouse IgG. At day 17, single-cell suspensions from tumor bearing lungs were FACS analyzed for percentage of infiltrated CD45+ cells (A), CD8 T cells and NK cells (B), tumor antigen AH1 (SPSYVYHQF (SEQ ID NO:5))-specific CD8 T cells (C), CD4 T cells that were Tim-3+PD-1+, Tim-3+ alone and PD-1+ alone (D), and CD11b+Ly6C+ monocytic myeloid-derived suppressor cells (F). Cell suspensions from tumor bearing lungs were stimulated with 1× cell stimulation cocktail for 5 hours and stained with antibodies to CD3, CD4 and IFN-γ or isotype controls (E). Shown are the ratios of Treg (CD4+Foxp3+) and MDSCs to CD8 T cells, CD4 T cells, and NK cells (G). Results are pooled from three independent experiments; *p<0.05, p<0.01, *p<0.001.

Figure 12A:
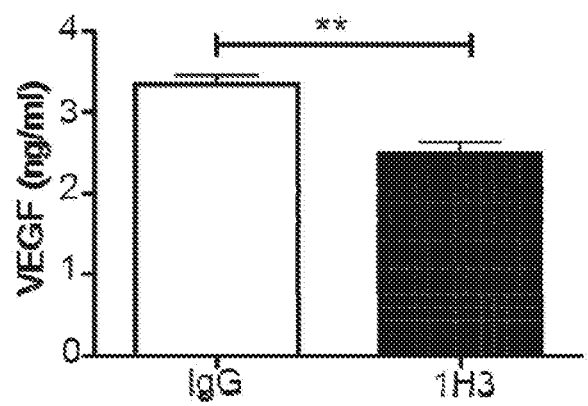
Figure 12B:
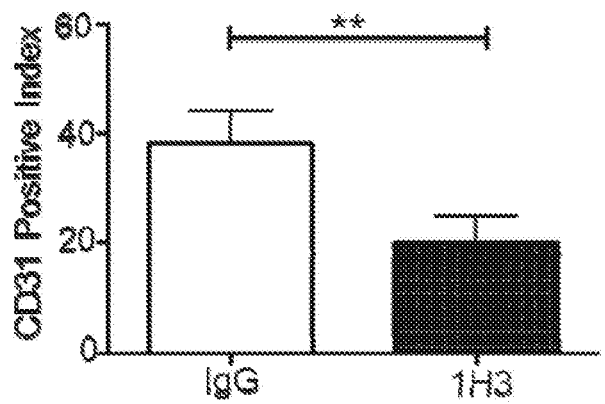
Figure 12C:
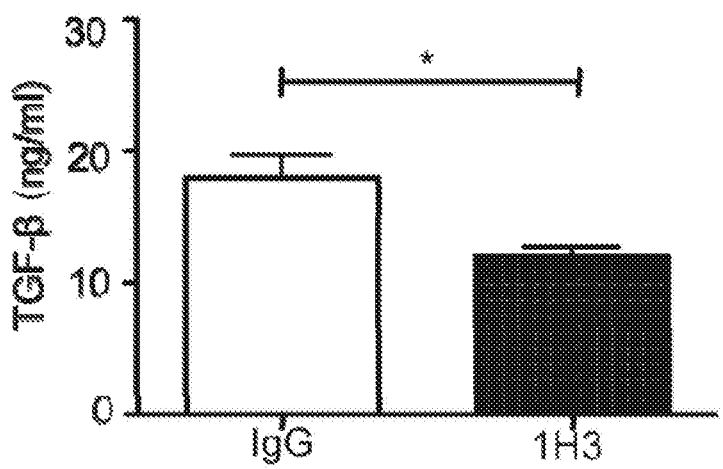

FIG. 12A-12C. The effects of 1H3 on tumor microenvironments. Paraffin sections of tumor bearing lungs from IgG- and 1H3-treated mice were stained with anti-VEGF and anti-CD31 antibodies. Hematoxylin was used for counter-staining. Total amount of VEGF and TGF-β from tumor bearing lungs were measured using ELISA. Each group contained 5 mice. *p<0.05; **p<0.01.

Figure 13A:
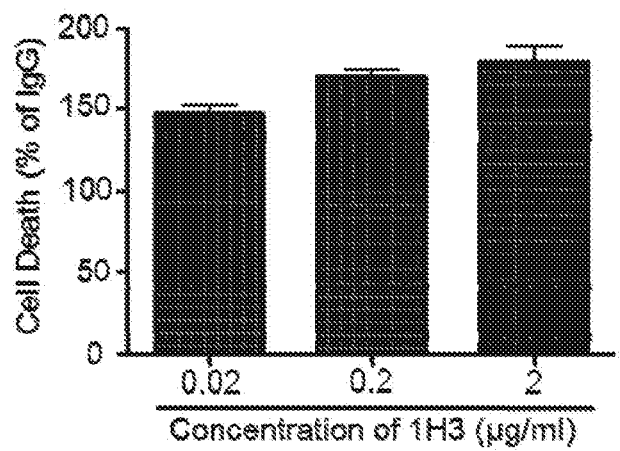
Figure 13B:
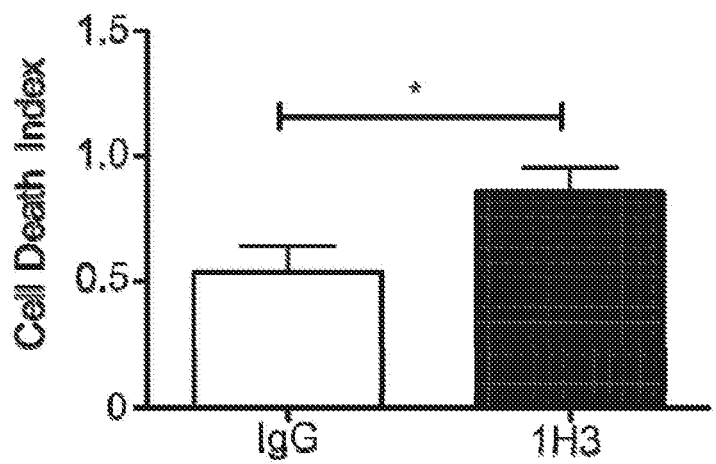
Figure 13C:
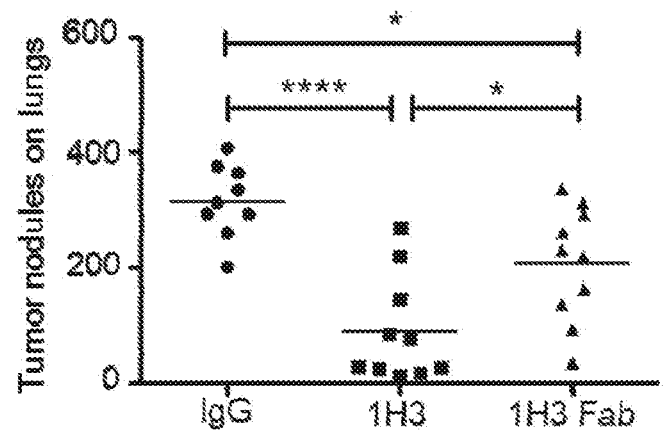

FIG. 13A-13C. Anti-tumor mechanisms of 1H3. (A) 1H3 kills tumor cells through antibody-dependent cellular cytotoxicity. B7x/CT26 cells labeled with CFSE and PKH-26 were incubated with splenocytes in the presence of various concentrations of mAb 1H3 or IgG. Percentages of tumor cell death induced by 1H3-mediated ADCC were normalized to those of control mouse IgG. Data are representative of two independent experiments in triplicates and shown as mean±SE. (B) BALB/c mice were iv injected with B7x/CT26 and then treated with 1H3 or control mouse IgG. After mice sacrifice at day 17, lung sections were subjected to the TUNEL assay. Normalized apoptotic staining was measured and compared. *p<0.05. (C) Comparison of therapeutic efficacies between 1H3 and its Fab. BALB/c mice were iv injected with B7x/CT26 cells at day 0 and then injected ip 200 μg/mouse with 1H3, Fab of 1H3, or control mouse IgG at day 1, 3, 7, 11 and 14. At day 17, tumor nodules in lungs were counted. Data were pooled from two independent experiments (n=9 or 10). *p<0.05; ****p<0.0001.

Figure 14A:
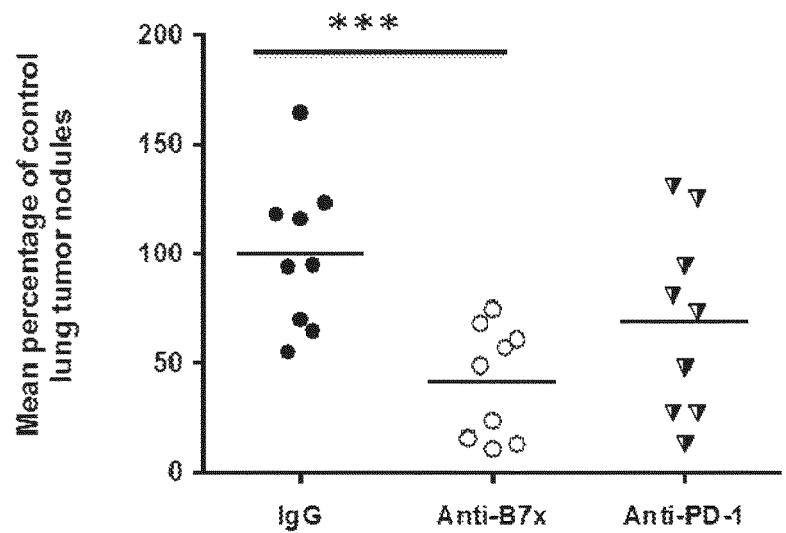
Figure 14B:
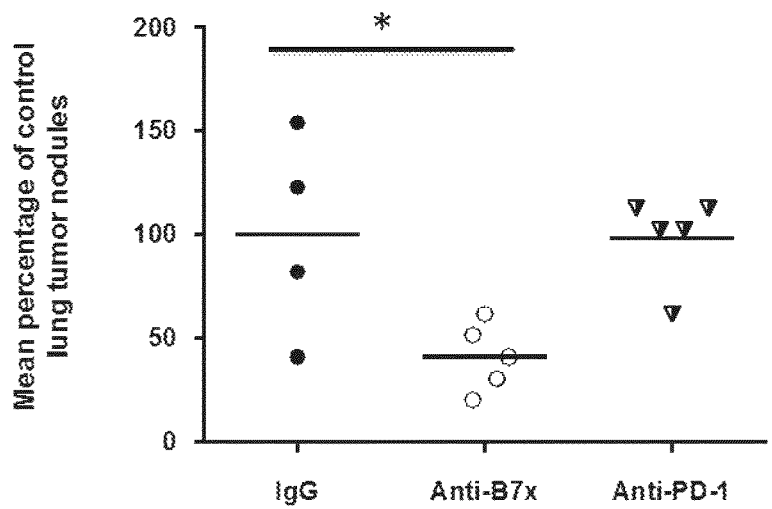

FIG. 14A-14B. Anti-B7x antibody therapy is better than anti-PD-1 antibody therapy in two lung metastasis of cancer models. (A) BALB/c mice were iv injected with B7x/CT26 tumor on day 0 and then ip injected with normal IgG (control), anti-B7x mAb 1H3, or anti-PD-1 mAb RMP1-14 on day 1,3,7,11, 14. On day 17, mice were sacrificed and numbers of lung tumor nodules were evaluated. Anti-B7x treatment reduced more than 58% of lung tumor nodules, ***P<0.001; whereas anti-PD-1 treatment reduced only 34% of lung tumor nodules and did not reach statistical significance. (B) BALB/c female mice were injected with B7x/4T1 tumor into the mammary fatpad on day 0 and then ip injected with normal IgG (control), anti-B7x mAb 1H3, or anti-PD-1 mAb RMP1-14 on day 8,11,13,15, 18. On day 20, mice were sacrificed and numbers of lung tumor nodules were evaluated. Anti-B7x treatment reduced more than 58% of lung tumor nodules, *P<0.05; whereas anti-PD-1 did not have an effect.

DETAILED DESCRIPTION OF THE INVENTION

The present invention provides a method for treating metastatic cancer in a patient having metastatic cancer or for preventing metastasis in a cancer patient at risk for metastasis comprising administering to the patient an antibody to B7x, or an active antibody fragment that binds B7x, in an amount effective to treat or prevent metastasis.

As used herein "metastasize" means, in regard to a cancer or tumor, to spread from one organ or tissue of a patient to another non-adjacent organ or tissue of the patient.

To "treat" a metastatic cancer means to reduce the number of metastases in an organ or tissue, and/or to kill metastatic tumor cells or tumor cells that are likely to metastasize, and/or to prevent or reduce the spread of cancerous cells from an original site in the body to another site in the body, and/or to inhibit the progression of metastatic cancer, and/or to prevent the reoccurrence of metastasis. Preferably, administration of the antibody or antibody fragment decreases the number of tumor nodules in the patient. Preferably, administration of the antibody or antibody fragment increases the patient's survival time.

Various diagnostic procedures have been developed to identify cancer patients at risk for metastasis. See, for example, U.S. Patent Application Publication Nos. 2008/0138805, 2011/0059470 and 2011/0059470, the contents of which are herein incorporated by reference.

The cancer can be, for example, a cancer of the skin, breast, pancreas, prostate, ovary, kidney, esophagus, gastrointestinal tract, colon, brain, liver, lung, head and/or neck. In a preferred embodiment, the cancer is lung cancer.

Preferably, the tumor in the patient expresses B7x or overexpresses B7x compared to healthy tissue, for example, in comparison to healthy tissue of the breast, pancreas, prostate, ovary, kidney, gastrointestinal tract, colon, brain, liver, lung, head and/or neck. The level of B7x expression in the tumor can be determined, for example, using immunohistocytochemistry on a tissue sample obtained from the tumor (e.g., Zang et al.[2,3]). B7x expression can also be determined by measuring expression of B7x mRNA in the tumor sample, for example by Northern blot hybridization (e.g., Allison et al.[16]).

Accordingly, the invention also provides a method for treating metastatic cancer in a patient having metastatic cancer or for preventing metastasis in a cancer patient at risk for metastasis comprising determining the level of B7x expression in a tumor sample from the patient, and if B7x is over-expressed in the tumor sample compared to the level of B7x expression in healthy tissue, administering to the patient an antibody to B7x, or an active antibody fragment that binds B7x, in an amount effective to treat or prevent metastasis. The method can further comprise obtaining a tumor sample from the patient.

As used herein, the term "antibody" refers to complete, intact antibodies. A "fragment" of an antibody refers to a fragment that bind the antigen of interest, B7x. Antibody fragments include, but are not limited to, F(ab')$_2$ and Fab' fragments and single chain antibodies. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. Complete, intact antibodies include, but are not limited to, polyclonal antibodies, monoclonal antibodies such as murine monoclonal antibodies, chimeric antibodies, human antibodies, and humanized antibodies.

Various forms of antibodies may be produced using standard recombinant DNA techniques. For example, "chimeric" antibodies may be constructed, in which the antigen binding domain from an animal antibody is linked to a human constant domain (an antibody derived initially from a nonhuman mammal in which recombinant DNA technology has been used to replace all or part of the hinge and constant regions of the heavy chain and/or the constant region of the light chain, with corresponding regions from a human immunoglobulin light chain or heavy chain). Chimeric antibodies reduce the immunogenic responses elicited by animal antibodies when used in human clinical treatments. In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted. For example, human IgG Fc can be used to replace the mouse Fc part of a monoclonal antibody.

The antibody can be, e.g., any of an IgA, IgD, IgE, IgG, or IgM antibody. The IgA antibody can be, e.g., an IgA1 or an IgA2 antibody. The IgG antibody can be, e.g., an IgG1, IgG2, IgG2a, IgG2b, IgG3 or IgG4 antibody. A combination of any of these antibodies subtypes can also be used. One consideration in selecting the type of antibody to be used is the desired serum half-life of the antibody. IgG has a serum half-life of 23 days, IgA 6 days, IgM 5 days, IgD 3 days, and IgE 2 days[15]. Another consideration is the size of the antibody. For example, the size of IgG is smaller than that of IgM allowing for greater penetration of IgG into tumors. Preferred antibodies include IgG1 monclonal antibodies.

The antibodies and antibody fragments of the present invention are designed by humans and made outside of the human body. The antibodies and antibody fragments are specific for B7x, but not for other B7 family members (i.e., B7-1, B7-2, B7h, PD-L1, PD-L2, and B7-H3).

Preferred antibodies include monoclonal antibodies 1H3 and 12D11. Preferred antibodies include monoclonal antibodies having a light and/or heavy chain the same as the light and/or heavy chain of 1H3 or 12D11. The heavy and/or light chains can contain conservative amino acid sequence modifications that do not significantly affect the binding characteristics of the antibody. Preferred antibodies include monoclonal antibodies that bind to the same epitope on B7x as 1H3 or 12D11. Preferred antibodies include monoclonal antibodies that block the interaction between B7x and its receptor. Preferred antibodies include antibodies that kill tumor cells through antibody-dependent cell-mediated cytotoxicity. Preferably, the antibody or antibody fragment blocks inhibition of T cell function by B7x. Preferably, the antibody or antibody fragment blocks interaction between cancer-expressed B7x and activated T cells. Preferably, the antibody or antibody fragment binds cancer-expressed B7x and kill cancer cells.

The antibodies and antibody fragments used for therapy in the present invention do not include antibody-partner molecule conjugates, where the partner can be, for example, one or more of a drug, toxin, radioisotope, therapeutic agent, or marker agent. The antibodies and antibody fragments of the present invention are therapeutically effective without the need for another therapeutic agent conjugated to the antibody or fragment. Antibodies and antibody fragments that are used for determining the expression of B7x expression in a tumor sample from a patient can be conjugated to a marker, such as, for example, a fluorescent marker or a radioisotope marker.

In one embodiment, the antibody or antibody fragment is the sole therapeutic anti-cancer agent administered to the patient. In another embodiment, the antibody or antibody fragment can be administered in combination with another anti-cancer agent that is not bound to the antibody or antibody fragment. Anti-cancer agents include, but are not limited to, an antibody against CTLA-4 (YERVOY®); an antibody against PD-1 (MDX-1106); an anti-epidermal growth factor receptor (EGFR) agent such as, e.g., panitumumab, the anti-EGFR antibody cetuximab (Erbitux®), and the EGFR tyrosine kinase (TK) inhibitors gefitinib (Iressa®) and erlotinib (Tarceva®); an alkylating agent such as, e.g., cisplatin, carboplatin, oxaliplatin, nedaplatin, satraplatin, triplatin tetranitrate, mechlorethamine, cyclophosphamide, chlorambucil and ifosfamide; paclitaxel and docetaxel; and topoisomerase inhibitors such as, e.g., irinotecan, topotecan, amsacrine, etoposide, etoposide phosphate and teniposide.

The antibody or antibody fragment can be screened for efficacy using, e.g., procedures set forth herein in Experimental Details.

The antibody or antibody fragment can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutical composition can be formulated for administration by any method known in the art, including but not limited to, direct administration to a tumor, parenteral administration, intravenous administration, and intramuscular administration.

The patient can be a human or another animal.

Human and mouse B7x have the amino acid and nucleic sequences indicated below.

```
Human B7x amino acid sequence (SEQ ID NO: 1):
MASLGQILFWSIISIIIILAGAIALIIGFGISGRHSITVTTVASAGNIGEDGILSCTFEPDIKLSDIVI

QWLKEGVLGLVHEFKEGKDELSEQDEMERGRTAVFADQVIVGNASLRLKNVQLTDAGTYKCYIITSKGK

GNANLEYKTGAFSMPEVNVDYNASSETLRCEAPRWFPQPTVVWASQVDQGANFSEVSNTSFELNSENVT

MKVVSVLYNVTINNTYSCMIENDIAKATGDIKVTESEIKRRSHLQLLNSKASLCVSSFFAISWALLPLS

PYLMLK

Mouse B7x amino acid sequence (SEQ ID NO: 2):
MASLGQIIFWSIINIIIILAGAIALIIGFGISGKHFITVTTFTSAGNIGEDGTLSCTFEPDIKLNGIVI

QWLKEGIKGLVHEFKEGKDDLSQQHEMFRGRTAVFADQVVVGNASLRLKNVQLTDAGTYTCYIRTSKGK

GNANLEYKTGAFSMPEINVDYNASSESLRCEAPRWFPQPTVAWASQVDQGANFSEVSNTSFELNSENVT

MKVVSVLYNVTINNTYSCMIENDIAKATGDIKVTDSEVKRRSQLQLLNSGPSPCVFSSAFVAGWALLSL

SCCLMLR.

Nucleic acid encoding Human B7x (SEQ ID NO: 3):
atggcttccc tggggcagat cctcttctgg agcataatta gcatcatcat tattctggct    60
ggagcaattg cactcatcat tggctttggt atttcaggga gacactccat cacagtcact   120
actgtcgcct cagctgggaa cattggggag gatggaatcc tgagctgcac ttttgaacct   180
gacatcaaac tttctgatat cgtgatacaa tggctgaagg aaggtgtttt aggcttggtc   240
catgagttca agaaggcaa agatgagctg tcggagcagg atgaaatgtt cagaggccgg    300
acagcagtgt ttgctgatca agtgatagtt ggcaatgcct ctttgcggct gaaaaacgtg   360
caactcacag atgctggcac ctacaaatgt tatatcatca cttctaaagg caaggggaat   420
gctaaccttg agtataaaac tggagccttc agcatgccgg aagtgaatgt ggactataat   480
gccagctcag agaccttgcg gtgtgaggct ccccgatggt tcccccagcc cacagtggtc   540
tgggcatccc aagttgacca gggagccaac ttctcggaag tctccaatac cagctttgag   600
ctgaactctg agaatgtgac catgaaggtt gtgtctgtgc tctacaatgt tacgatcaac   660
aacacatact cctgtatgat tgaaaatgac attgccaaag caacagggga tatcaaagtg   720
acagaatcgg agatcaaaag gcggagtcac ctacagctgc taaactcaaa ggcttctctg   780
tgtgtctctt ctttctttgc catcagctgg gcacttctgc ctctcagccc ttacctgatg   840
ctaaaataa                                                          849

Nucleic acid encoding mouse B7x (SEQ ID NO: 4):
atggcttcct tggggcagat catcttttgg agtattatta acatcatcat catcctggct    60
ggggccatcg cactcatcat tggctttggc atttcaggca agcacttcat cacggtcacg   120
accttcacct cagctgggaa cattggagag gacgggaccc tgagctgcac ttttgaacct   180
```

```
                                           -continued
gacatcaaac tcaacggcat cgtcatccag tggctgaaag aaggcatcaa aggtttggtc    240
cacgagttca aagaaggcaa agacgacctc tcacagcagc atgagatgtt cagaggccgc    300
acagcagtgt ttgctgatca ggtggtagtt ggcaatgctt ccctgagact gaaaaacgtg    360
cagctcacgg atgctggcac ctacacatgt tacatccgca cctcaaaagg caaagggaat    420
gcaaacctag agtataagac cggagccttc agtatgccag agataaatgt ggactataat    480
gccagttcag agagtttacg ctgcgaggct cctcggtggt tcccccagcc cacagtggcc    540
tgggcatctc aagtcgacca aggagccaac ttctcagaag tctcgaacac cagctttgag    600
ttgaactctg agaatgtgac catgaaggtc gtatctgtgc tctacaatgt cacaatcaac    660
aacacatact cctgtatgat tgaaaatgac attgccaaag ccactgggga catcaaagtg    720
acagattcag aggtcaaaag gcggagtcag ctgcagctgc tcaactccgg gccttccccg    780
tgtgtttttt cttctgcctt tgcggctggc tgggcgctcc tatctctctc ctgttgcctg    840
atgctaagat ga                                                        852
```

The invention further provides an antibody to B7x, or an active antibody fragment that binds B7x, for use in a method of treatment of metastatic cancer in a patient having metastatic cancer or for use in a method of prevention of metastasis in a cancer patient at risk for metastasis. The invention still further provides an antibody to B7x, or an active antibody fragment that binds B7x, for use in a method of determining if B7x is over-expressed in a tumor sample from a patient compared to healthy tissue, and for use in a method of treatment of metastatic cancer in a patient having metastatic cancer or for use in a method of prevention of metastasis in a cancer patient at risk for metastasis, where B7x is over-expressed in a tumor sample from the patient.

Preferably, the antibody or antibody fragment binds to the IgV domain of B7x and/or to amino acid residues 35-148 of B7x (e.g., to amino acids 35-148 of SEQ ID NO:1).

Preferably, administration of the antibody or antibody fragment prevents the reoccurrence of a tumor in the patient.

The invention also provides a method of producing a monoclonal antibody to B7x comprising immunizing a B7x knockout mouse with a B7x-Ig fusion protein, generating a hybridoma from spleen cells from the mouse, and testing supernatant from the hybridoma for its ability to react with immobilized B7x-Ig or a cell line expressing B7x, but not with control Igs or cell lines expressing other B7 family members, to identify a monoclonal antibody to B7x. Control Igs include, for example, other B7-Igs such as B7-1-Ig, B7-2-Ig, B7h-Ig, PD-L1-Ig, PD-L2-Ig and B7-H3-Ig. Cell lines expressing other B7 family members include, for example, cell lines expressing B7-1, B7-2, B7h, PD-L1, PD-L2 and/or B7-H3. Supernatant from the hybridoma can be tested using, for example, an enzyme-linked immunosorbent assay (ELISA) or a fluorescence-activated cell sorter (FACS). The method can further comprise purifying the antibody from the supernatant. The method can further comprise generating a B7x knockout mouse. A B7x knockout mouse can be generated, for example, as follows. 3.4- and 5.2-kb of B7x genomic fragments can be cloned into a knock-out vector as 5' and 3' arms. The vector can then be electroporated into embryonic stem cells. An embryonic stem cell clone heterozygous for the mutant can then be microinjected into blastocysts from normal mice. Chimeric males can be crossed with females to give rise to the mutant B7x allele.

The invention further provides a method of screening monoclonal antibodies to B7x to identify an antibody that inhibits tumor growth in vivo, the method comprising injecting tumor cells expressing B7x on their cell surface into a mouse to induce a tumor in the mouse, and injecting a monclonal antibody to B7x into the mouse to identify an antibody that inhibits tumor growth in vivo. B7x can be stably expressed on tumor cells using, for example, a retroviral expression vector. B7x expression on the surface of tumor cells can be confirmed, for example, with antibody to B7x using a fluorescence-activated cell sorter (FACS). Preferably, the antibody inhibits metastasis.

The invention further provides a method for preventing reoccurrence of a tumor in a patient comprising administering to the patient an antibody to B7x, or an active antibody fragment that binds B7x, in an amount effective to prevent reoccurrence of a tumor in a patient. Therapy with the antibody or antibody fragment may, for example, increase local infiltration of anti-tumor immune cells such as CD8 T cells including tumor antigen-specific CD8 T cells, NK cells, and IFN-γ-producing CD4 T cells. In addition, or instead, the therapy may, for example, reduce local infiltration of immunosuppressive myeloid-derived suppressor cells (MDSCs).

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example I

Cancer-Expressed B7x Promotes Metastatic Cancer Progression

The over-expression of B7x by tumor cells raises the possibility that it might provide a mechanism by which tumor cells avoid destruction mediated by tumor-reactive T cells and other immune cells. This is an interesting possibility for two reasons. The first is that high levels of B7x expression might facilitate tumor progression, and it may therefore provide a useful prognostic marker to predict outcome. The second is that B7x may be useful therapeutic target for checkpoint blockade with immunotherapy.

In order to develop new drugs with B7x as a target, a mouse system was first developed in which cancer-expressed B7x can promote cancer progression and drugs can be screened. Two lung metastatic cancer models were developed in which the expression of B7x on CT26 and MC38 cancer cells significantly increased mortality in mice (FIG. 2).

Like most tumor cell lines which permanently lose endogenous B7x protein expression after in vitro culture, two tumor lines CT26 and MC38 are B7x negative and are able to induce lung metastasis when direct injected intravenously (iv) through the tail vein. A retroviral expression vector B7x/MSCV was generated to make CT26 and MC38 stably expressing B7x. Syngeneic Balb/c mice were then iv injected with $1\times10^5$/per-mouse of CT26 or B7x/CT26, and survival kinetics were monitored. Mice injected with CT26 started to die at day 26 and half were still alive at day 50, whereas mice injected with B7x/CT26 started to die at day 21 and were all dead at day 33 (FIG. 2A). In a parallel study, syngeneic C57BL/6 started to die at day 44 after iv injection with $1\times10^5$/per-mouse of MC38 and 37% were still alive at day 100, whereas mice iv injected with $1\times10^5$/per-mouse of B7x/MC38 started to die at day 33 and were all dead at day 80 (FIG. 2B).

In a subsequent experiment, Balb/c mice were iv injected with $1\times10^5$/per-mouse of CT26 or B7x/CT26 and killed on day 20 to determine tumor nodules in the lung. FIG. 3 showed that B7x/CT26 resulted in much more tumor nodules in the lung than CT26. Collectively, these results demonstrate that expression of B7x on tumor cells accelerates disease progression in vivo.

Host Cell-Expressed B7x Promotes Expansion of Immune Suppressor Cells within the Tumor Microenvironment Some tissue cells express very low level of B7x, so B7x gene knock-out mice were used to dissect the role of host B7x in cancer immune responses. Naïve B7x−/− mice were normal and healthy. B7x-negative 4T1 cells ($1\times10^5$/per mouse) were injected iv into both B7x−/− (on pure BALB/c background) and wildtype BALB/c mice, and tumor progression and tumor nodules in lungs were monitored. 4T1 was B7x negative in vitro and in vivo by RT-PCR (data not shown). At day 18, B7x−/− mice had many fewer tumor nodules in lungs than wildtype control (FIG. 4A). All wildtype mice were dead at day 36, whereas 33% of B7x−/− mice were still alive at day 72 (FIG. 4B). These results reveal that host B7x promotes lung metastasis of cancer and that removal of host B7x protects mice from this disease. As more than 30% of B7−/− mice survived lung metastasis, these surviving B7x−/− mice were re-challenged with a higher dose ($2\times10^5$/per mouse) of 4T1, and their survival was monitored. Remarkably, none of these mice died (FIG. 4B). At day 140 after primary injection, these mice were sacrificed and histological examination demonstrated that lungs of these mice did not have tumor. These results suggest that B7x deficiency not only protects mice from lung metastasis but also helps to develop strong immune memory of sufficient magnitude to completely eliminate the tumor.

Flow cytometric analysis was used to identify host cells of tumor infiltrates that are involved in anti-tumor responses. Wildtype mice had significantly more Foxp3+CD4+ regulatory T cells (Treg) and CD11b+Ly6G+ myeloid-derived suppressor cells (MDSC) in the lung than B7x−/− mice on day 18 after iv injection of 4T1 tumor cells (FIG. 4C). Recent work has revealed that Treg[11,12] and MDSC[13,14] are two major cell populations capable of suppressing immune responses. The present results suggest that host cell-expressed B7x promotes expansion of immune suppressor cells within the tumor microenvironment.

Generation of Monoclonal Antibodies Recognizing Both Human and Mice B7x

Monoclonal antibodies (mAbs) were generated against both human and mice B7x from B7x gene knock-out mice. Briefly, B7x knock-out mice were immunized with B7x-Ig fusion protein and their spleen cells were used for generation of hybridomas. Thirty-two independent clones were obtained whose supernatant reacted with immobilized B7x-Ig, but not control Ig, in a standard ELISA. Eight of these were selected for further study. The specificity of these hybridomas for B7x was confirmed by flow cytometry staining cell lines overexpressing B7x, but not cells expressing other B7 family members (B7-1, B7-2, B7h, PD-L1, PD-L2, and B7-H3).

Monoclonal Antibodies Inhibit Metastatic Cancer Progression In Vivo

Four mAbs [clones: 37G9 (IgG2b), 1H3 (IgG1), 12D11 (IgG1), 19D6 (IgG1)] were purified and their therapeutic effects examined with B7x/CT26 lung metastatic cancer model. Syngeneic BLAB/c mice iv injected with $1\times10^5$/per-mouse of B7x/CT26 on day 0 and then i.p injected with 200m/per-mouse of each mAb on day 1,3,7,11,14, or PBS as the control. All mice were killed on day 17 and tumor nodules in each lung were examined. Two clones, 12D11 and 1H3, had very good therapeutic effects. Both mAbs were able to reduce more than 50% tumor nodules in the lung in such a robust metastatic cancer model (FIG. 5). The other two mAb clones (37G9 and 19D6) did not have significant therapeutic effects in vivo (data not shown), which is most likely due to the possibility that 37G9 and 19D6 are unable to block the interaction between B7x and its receptor(s).

Cancer-Expressed Human B7x Promotes Metastatic Cancer Progression In Vivo

To facilitate the translation of this research into clinical trials, another lung metastatic cancer model was developed in which the expression of human B7x on CT26 cancer cells significantly increased metastatic cancer progression in mice in vivo. A CT26 cell line, hB7x/CT26, was made that stably express human B7x on cell surface. Balb/c mice were iv injected with $1\times10^5$/per-mouse of CT26 or hB7x/CT26 and killed on day 17 to determine tumor nodules in the lung. FIG. 6 shows that hB7x/CT26 resulted in much more tumor nodules in the lung than CT26, 112.8 vs 23.8, demonstrating human B7x expressed on cancer cells can promote metastatic cancer progression in vivo. This system can be used to identify monoclonal antibodies that are suitable for human clinical trials.

Monoclonal Antibody Inhibits Human B7x-Expressed Metastatic Cancer Progression In Vivo A lung metastatic cancer model was developed in which the expression of human B7x on CT26 cancer cells (hB7x/CT26) significantly increased metastatic cancer progression in mice in vivo (FIG. 6). To further facilitate the translation of this research into clinical trials, it was determined whether mAbs were able to inhibit human B7x-expressed metastatic cancer progression in vivo. Syngeneic BLAB/c mice were iv injected with $1\times10^5$/per-mouse of hB7x/CT26 on day 0 and then i.p injected with 200 µg/per-mouse of mAb 1H3 on day 1,2,3,5,7,9,11,13,15, or PBS as the control. All mice were killed on day 17 and tumor nodules in each lung were examined. Monoclonal antibody 1H3 had very good therapeutic effects, and reduced more than 60% of tumor nodules in the lung in such a robust humanized metastatic cancer model (FIG. 7).

Monoclonal Antibody-Dependent Cell-Mediated Cytotoxicity mAbs were tested to determine whether they were able to act through antibody-dependent cell-mediated cytotoxicity (ADCC). B7x/CT26 tumor cell as target cells, antibodies (0.2 µg/ml), and spleen cells from syngeneic BLAB/c mice as effector cells were incubated together at 37° C. for 4 hours, and then tumor cells were analyzed by flow cytometry. Compared to the control normal IgG, three (1H3, 15D2, 12D11) out of four mAbs significantly killed B7x-expressed CT26 tumor cells (FIG. 8). These results indicate that mAbs can kill B7x-positive tumor cells through ADCC.

B7x Protein is not Detected in Antigen Presenting Cells and T Cells

B7x protein is not detected in antigen-presenting cells (APC) and T cells in both human and mice, as presented in Table 1.

TABLE 1

B7x protein is not detected in APCs and T cells before and after stimuli.

| Immune cells | Stimulation and disease models |
|---|---|
| Human | |
| Dendritic cells | CD40L, LPS, PMA+ ionomycin, cytokine cocktail |
| Langerhans cells | CD40L, cytokine cocktail |
| Monocytes | LPS + IFN-γ |
| B cells | LPS, PMA+ ionomycin |
| T cells | PHA, PMA+ ionomycin |
| Mouse | |
| Dendritic cells | LPS, IL-4, IFN-γ, IL-10, TNF-α, 4T1 cancer, S. pneumoniae infection, B. malayi infection, |
| Macrophages | Thioglycolate, IL-4, LPS + IFN-γ, IL-6 + IL-10, TGF-β, Treg, 4T1 cancer, S. pneumoniae infection, B. malayi infection, |
| B cells | LPS, anti-IgM F(ab')2, PMA+ ionomycin, 4T1 cancer, S. pneumoniae infection |
| T cells | ConA, anti-CD3, PMA+ ionomycin, 4T1 cancer, S. pneumoniae infection Th1, Th2, Treg |

B7x protein was examined by flow cytometry with specific monoclonal or polyclonal Abs.

Mechanisms of Treatment for Cancers

The present results show that 1) cancer-expressed mice B7x promotes metastatic cancer progression in two mice models and that monoclonal antibodies can inhibit metastatic cancer progression in vivo, demonstrating that blockage of cancer-associated B7x can be used as a novel treatment for metastatic cancers; and 2) human B7x expressed on cancer cells can also promote metastatic cancer progression in vivo and that a monoclonal antibody can inhibit human B7x-expressing metastatic cancer progression in vivo, demonstrating that blockage of cancer-associated human B7x can be used as a novel treatment for metastatic cancers. There are three possible mechanisms by which this treatment can inhibit metastatic cancer progression in vivo (see FIG. 9): (A) antibodies block the interaction between cancer-expressed B7x and activated T cells, therefore increasing T cell-mediated immunity against cancer; (B) antibodies bind cancer-expressed B7x and kill cancer cells; and (C) antibodies block very low level of B7x expressed by some tissue cells, therefore inhibiting the expansion of regulatory T cells (Treg) and myeloid-derived suppressor cells (MDSC) within the tumor microenvironment.

Discussion

The present technology has enormous market and clinical potential for at least three reasons. 1) B7x is expressed in many human cancers, so it is an excellent therapeutic target for human cancers such as, for example, cancers of the lung, pancreas, kidney, brain, gut, prostate, breast, esophagus, skin, thyroid, stomach and ovary. 2) More than 90% of cancer patients die from metastasis; therefore, therapies for metastasis are desperately needed. 3) The antibodies describe herein recognize both human and mice B7x, so these antibodies can be used in clinical trials.

Like B7x, CTLA-4 and PD-1 are two members of the B7/CD28 family. An antibody against CTLA-4 (YERVOY® from Bristol-Myers Squibb Company) was approved by the FDA in March 2011 as a new drug for metastatic melanoma. Antibodies against PD-1 (MDX-1106) are in phase I clinical trials. These existing technologies work by blockade of the B7/CD28 family members CTLA-4 and PD-1 on activated T cells, so they increase immunity against cancer but also induce autoimmune diseases. In contrast, the present technology works by blockade of B7x on cancer cells, so as to increase specific immunity against cancer without inducing autoimmune diseases.

Example II

Interaction of mAbs with B7x IgV Domain

Binding rate constants were estimated and corresponding equilibrium affinity constants ($K_D$s) derived for the interactions of mAbs with recombinant murine B7x ectodomain, as well as murine and human B7x-IgV through surface plasmon resonance (SPR). Antibodies 1H3, 12D11 and 15D12 strongly interacted with all of these proteins, with dissociation constants summarized in Table 2.

Anti-B7x mAb Therapy in Mouse B7x-Expressing Tumor Models

To develop a functional screening system for immunotherapy, tumor cell lines expressing cell surface B7x were established, since most tumor lines were B7x protein negative. Mouse colon carcinoma CT26 (which were B7x negative) and B7x/CT26 (which expressed mouse B7x on the surface) were intravenously (iv) injected into syngeneic BALB/c mice to induce experimental lung metastasis. By day 17 after injection, the average number of lung tumor nodules in the B7x/CT26 group was ~3.5 fold higher than that in the CT26 group, suggesting that the expression of B7x on CT26 tumor cells significantly promotes tumor progression in vivo.

Figure 10A:
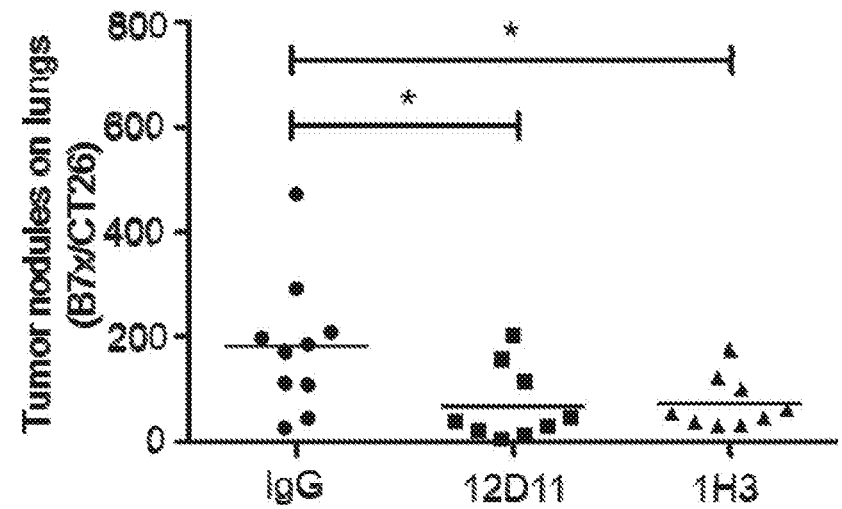
Figure 10B:
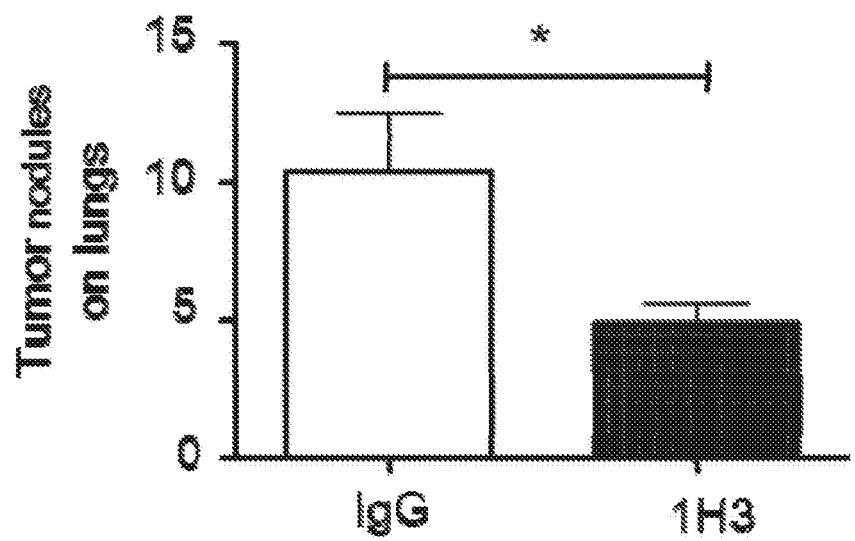

The in vivo therapeutic effects of B7x-specific mAbs were screened in the B7x/CT26-induced pulmonary metastasis model. B7x/CT26 cells were iv injected into BALB/c mice followed by intraperitoneal (ip) injection of anti-B7x mAbs. By day 17, lung tumor nodules were examined. Two mAbs, 1H3 and 12D11, significantly reduced ~60% of tumor nodules in lungs. The 4T1 mammary carcinoma cell line that spontaneously metastasizes to the lung[20] was tried next. 1H3 treatment significantly reduced primary tumor-induced metastatic tumor nodules in the lung (FIG. 10B).

Anti-B7x mAb Therapy in a Human B7x-Expressing Tumor Model

Figure 10C:
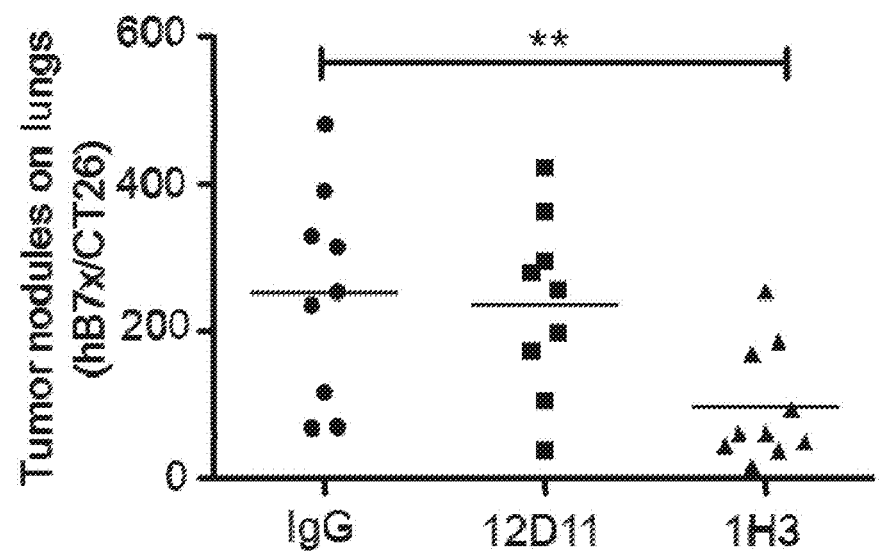

Since both 1H3 and 12D11 recognize human B7x (Table 2), the therapeutic effects of these two mAbs were tested in a human B7x-expressing tumor model in vivo using hB7x/CT26, which expressed human B7x on mouse CT26. Like mouse B7x, the expression of human B7x on CT26 markedly increased tumor nodules in the lung. Mice were iv injected with hB7x/CT26 and then treated with 1H3 or 12D11. On day 17, the average numbers of lung tumor nodules in 1H3-treated and 12D11-treated groups were 97 and 236, respectively, whereas the number in control group was 251 (FIG. 10C). Furthermore, 1H3 could recognize B7x expression on human colon and ovary cancers through immunohistochemistry. These results suggest that human B7x promoted tumor growth in vivo and that mAb 1H3 recognized human B7x and inhibited human B7x expressing tumor progression in vivo. Since 1H3 inhibited both human and mouse B7x-mediated tumor progression, it was used for the subsequent experiments.

1H3 mAb-Treated Mice Generate Memory Response and Survive B7x/CT26 Rechallenge

Figure 10D:
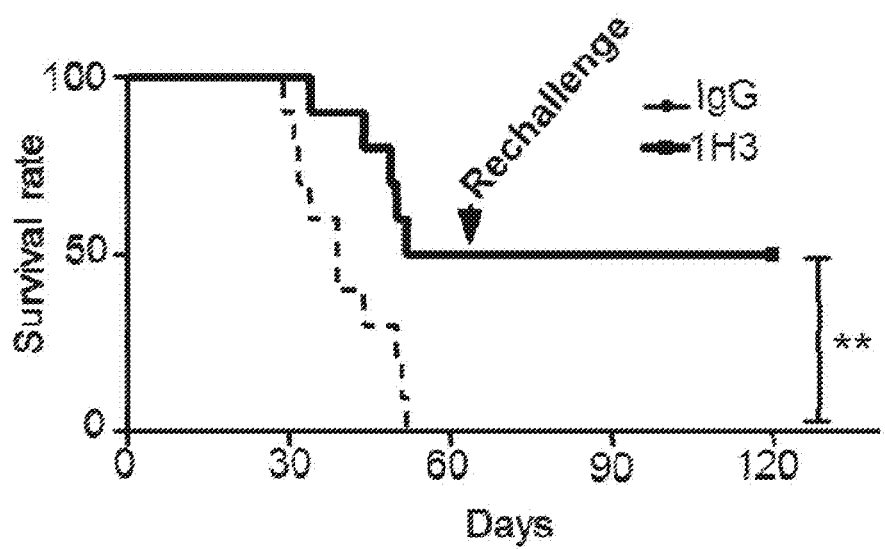

The effect of 1H3 on the survival of mice bearing B7x/CT26 tumors was investigated. In agreement with the lung tumor nodule results, 1H3 treated mice had a significantly lower mortality than control IgG-treated mice. By day 60 post-injection of tumor, 100% of IgG-treated mice were dead, whereas half of 1H3-treated mice remained alive (FIG. 10D). Then, it was examined whether the surviving mice had generated a memory response to the tumor. These mice were rechallenged with the same number of B7x/CT26 cells, and all of them remained alive for the following 60 days. On day 120, mice were sacrificed and hematoxylin and eosin (HE) staining of lung sections from these mice showed they were free of tumor. These results suggest that the 1H3 treatment induced a memory response against the tumor.

Figure 11A:
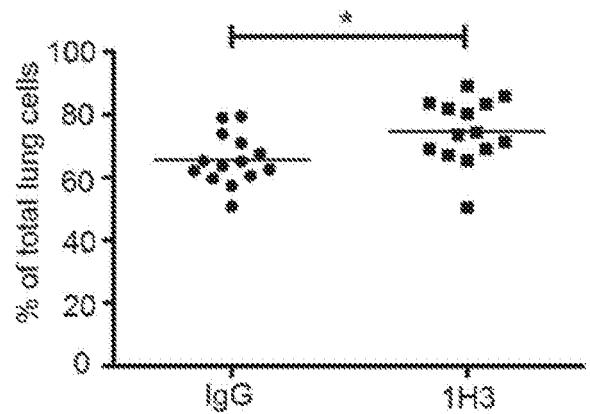
Figure 11B:
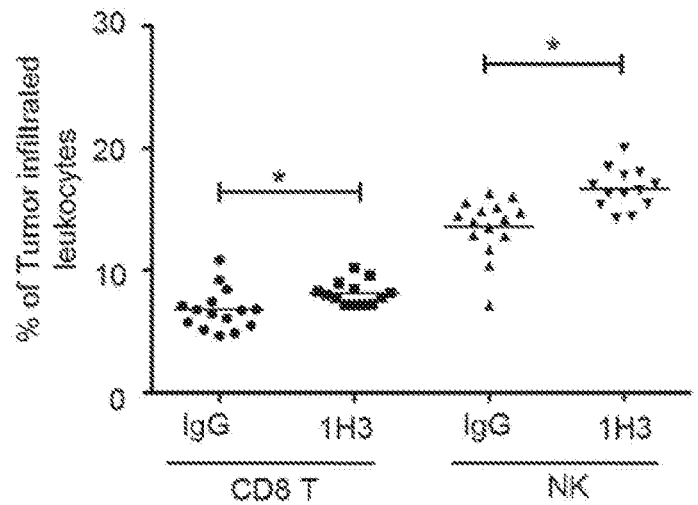
Figure 11C:
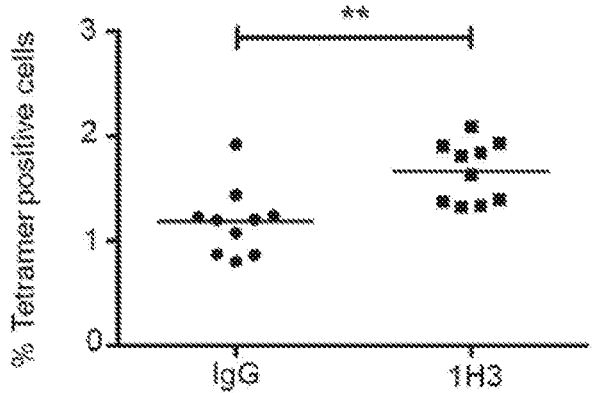
Figure 11D:
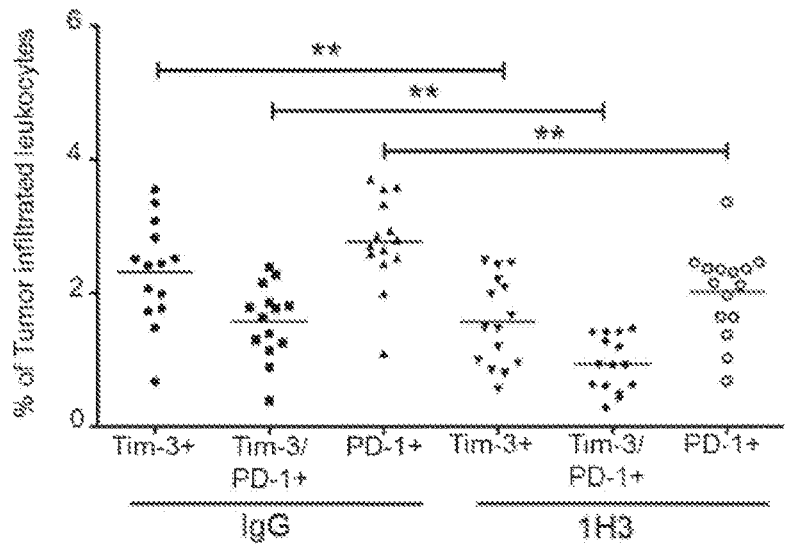
Figure 11E:
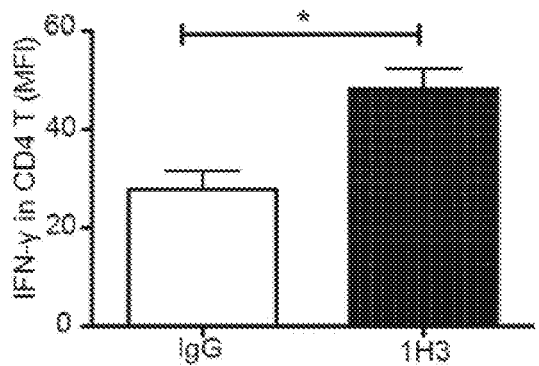

Anti-B7x Therapy Increases Infiltrating T and NK Cells and Decreases Infiltrating MDSCs within Tumors To dissect the therapeutic mechanisms of 1H3 treatment, single-cell suspensions were prepared from tumor-bearing lungs and immune cells were analyzed by flow cytometry. 1H3-treated mice had significantly higher percentages of CD45+ immune cell infiltrate than control IgG-treated mice (FIG. 11A). Among these CD45+ cells, the 1H3 treatment strongly increased infiltration of tumor by CD8 T cells and NK cells (FIG. 11B), two major types of anti-tumor immune cells. SPSYVYHQF/H(SEQ ID NO:5)-2L$^d$ tetramer was used to detect CD8 T cells specific for CT26 tumor antigen epitope AH1(amino acids 423-431 SPSYVYHQF (SEQ ID NO:5))[21,22]. In agreement with increased total CD8 T cells, 1H3 treatment increased the percentage of AH1-specific CD8 T cells (FIG. 11C). Recent studies identified the co-expression of Tim-3 and PD-1 (Tim-3+PD-1+) cells as a unique phenotype of exhausted T cells in melanoma and leukemia[23,24]. Therefore, the effect of 1H3 was examined on these two inhibitory receptors on CD4 T cells. 1H3-treated mice had significantly fewer CD4 T cells that were Tim-3+ PD-1+, Tim-3+ alone and PD-1+ alone (FIG. 11D), suggesting 1H3 treatment reduce the conversion of CD4 T cells from activated to exhausted state. Along with these finding, the 1H3 treatment enhanced CD4 T cells to produce IFN-γ (FIG. 11E), a critical cytokine for anti-tumor immunity.

Figure 11F:
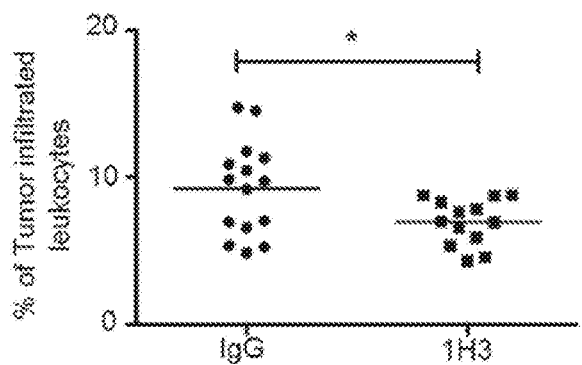
Figure 11G:
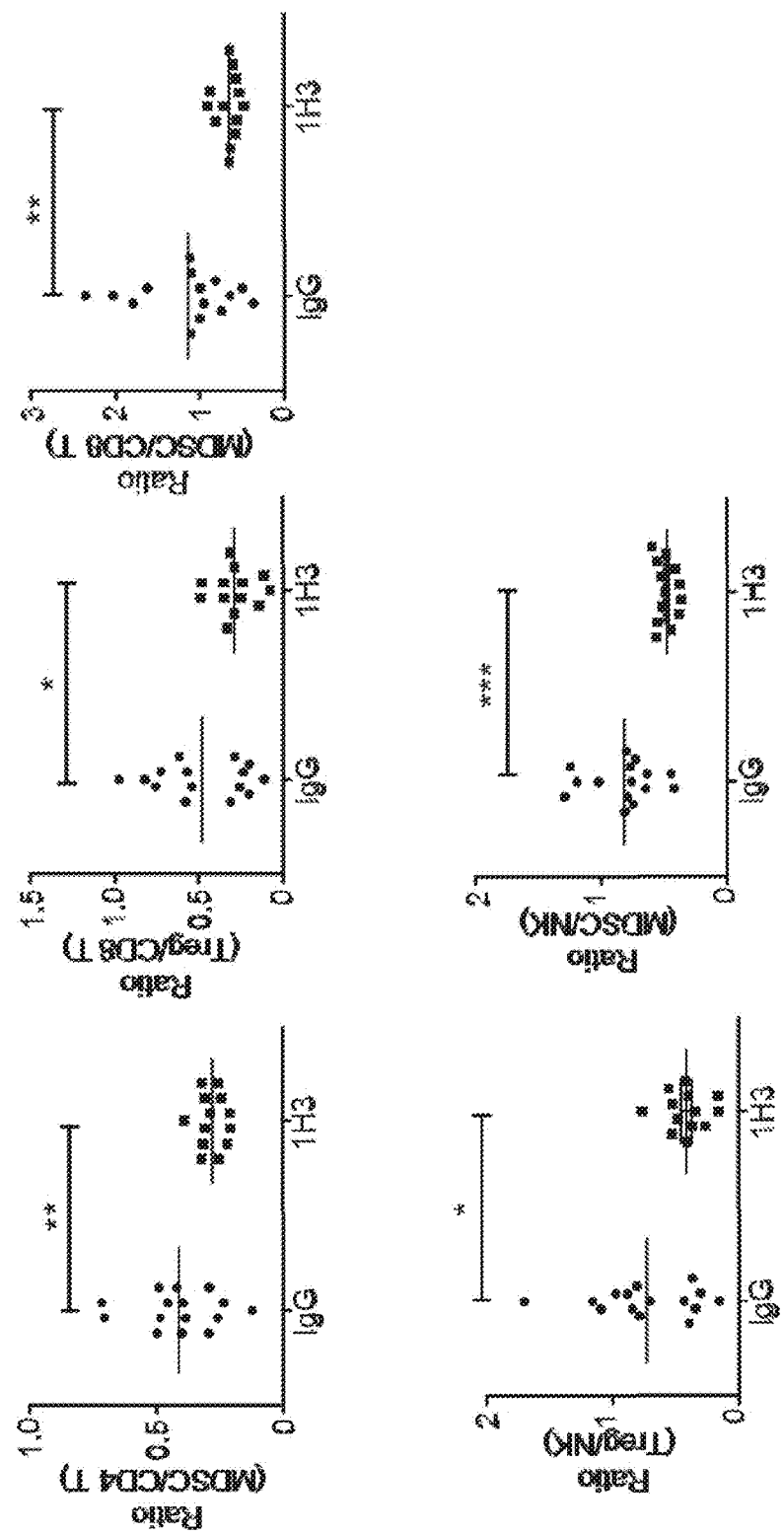

In the tumor microenvironment, suppression of effector T cell function is often driven by immunosuppressive cells. Therefore, the effect of 1H3 treatment on immunosuppressive cell infiltrates was investigated in tumor-bearing lungs. The treatment did not change the percentage of Foxp3+ CD4+ regulatory T cells (Tregs), but reduced CD11b+ Ly6C+ monocytic myeloid-derived suppressor cells (MDSCs) infiltrating tumor (FIG. 11F). The combined increase of CD8 T cell, NK and IFN-γ-producing CD4 T cells and reduction of MDSCs in the 1H3 treatment afforded a significantly lower ratio of the suppressive MDSCs and Tregs to effector anti-tumor immune cells (FIG. 11G).

Anti-B7x Therapy Decreases VEGF and TGF-β in the Tumor Microenvironment

VEGF stimulates angiogenesis in the tumor microenvironment and facilitates tumor growth and metastasis[25-28]. VEGF concentration in tumor-bearing lungs from 1H3 treated mice was significantly lower than that of control mice (FIG. 12A). Correspondingly, CD31 expression pattern in tumor vasculature revealed that the 1H3 treatment inhibited intratumor vasculature (FIG. 12B). The 1H3 treatment also lowered the concentration of TGF-β in tumor-bearing lungs (FIG. 12C), one of the key cytokines responsible for suppressing anti-tumor responses[29,30].

1H3 Kills Tumor Cells Through ADCC but not CDC

One way in which antibodies can eliminate virus-infected cells or tumor cells is via antibody-dependent cellular cytotoxicity (ADCC)[31-33]. It was examined whether 1H3 kills tumor cells through ADCC. 1H3 induced death of 50% more target cells compared to control IgG (FIG. 13A). In agreement with the in vitro ADCC result, significantly increased numbers of apoptotic cells were present in tumors from 1H3 treated mice (FIG. 13B). Antibodies can also eliminate tumor cells via complement-dependent cytotoxicity (CDC)[34]; however, 1H3 specific CDC activity could not be detected (data not shown).

1H3 Blocks B7x-Mediated T Cell Coinhibition

T cells proliferated vigorously when incubated with anti-CD3 and control Ig with more than 73% of T cells dividing. When T cells were incubated with anti-CD3 and B7x-Ig, significantly fewer T cells proliferated, with about 41% dividing. The presence of 1H3 in the system significantly neutralized B7x-mediated T cell coinhibition, as 1H3 increased T cell proliferation to >61%. Furthermore, Fab fragment of 1H3 had a similar neutralizing effect on B7x-induced T cell coinhibition. These results reveal that 1H3 can partially block B7x-mediated T cell coinhibition. To assess whether 1H3 therapy depends on ADCC and/or functional neutralization in vivo, therapeutic efficacies between 1H3 and its Fab (which cannot cause ADCC) were compared. Mice treated with the Fab had significantly fewer lung tumor nodules than did mice treated with control IgG, but had significantly more lung tumor nodules than did mice treated with 1H3 (FIG. 13C). Taken together, these results suggest that 1H3 inhibits tumor growth through the combination of ADCC and functional neutralization.

TABLE 2

Surface plasmon resonance measurements.

| mAb | $k_{on}$ (M$^{-1}$·s$^{-1}$) | $k_{off}$ (s$^{-1}$) | $K_D$ (nM) |
| --- | --- | --- | --- |
| murine B7x (IgV domain) | | | |
| 1H3 | 2.455(4)$^a$ × 10$^6$ | 0.001248(7) | 0.508(3) |
| 12D11 | 2.140(4) × 10$^6$ | 0.001341(8) | 0.627(4) |
| 15D12 | 1.790(3) × 10$^6$ | 0.001135(7) | 0.634(4) |
| murine B7x | | | |
| 1H3 | 6.71(3) × 10$^5$ | 0.001298(7) | 1.94(1) |
| 12D11 | 6.62(4) × 10$^5$ | 0.001177(7) | 1.78(1) |
| 15D12 | 4.40(3) × 10$^5$ | 0.001095(6) | 2.49(2) |
| human B7x (IgV domain) | | | |
| 1H3 | 2.53(2) × 10$^5$ | 0.00917(4) | 36.2(3) |
| 12D11 | 2.13(1) × 10$^5$ | 0.00928(3) | 43.5(3) |
| 15D12 | 1.388(7) × 10$^5$ | 0.01039(2) | 74.9(4) |

$^a$The value in parentheses denotes the standard error in the last digit

Example III

Anti-B7x Antibody Therapy is Better than Anti-PD-1 Antibody Therapy in Two Lung Metastasis of Cancer Models Anti-B7x antibody therapy was compared to anti-programmed cell death protein 1 (PD-1) antibody therapy in two lung metastasis of cancer models. Anti-PD-1 therapy is currently in phase 1 clinical trials in cancer patients.

In one model, BALB/c mice were iv injected with B7x/CT26 tumor on day 0 and then ip injected with normal IgG (control), anti-B7x mAb 1H3, or anti-PD-1 mAb RMP1-14 on day 1,3,7,11, 14. On day 17, mice were sacrificed and numbers of lung tumor nodules were evaluated. Anti-B7x treatment reduced more than 58% of lung tumor nodules, ***P<0.001; whereas anti-PD-1 treatment reduced only 34% of lung tumor nodules and did not reach statistical significance (FIG. 14A).

In a second model, BALB/c female mice were injected with B7x/4T1 tumor into the mammary fatpad on day 0 and then ip injected with normal IgG (control), anti-B7x mAb 1H3, or anti-PD-1 mAb RMP1-14 on day 8,11,13,15, 18. On day 20, mice were sacrificed and numbers of lung tumor nodules were evaluated. Anti-B7x treatment reduced more than 58% of lung tumor nodules, *P<0.05; whereas anti-PD-1 did not have an effect (FIG. 14B).

REFERENCES

1. Zang, X., et al. B7x: a widely expressed B7 family member that inhibits T cell activation. *Proc. Natl. Acad. Sci. U S. A.* 100, 10388-10392 (2003).
2. Zang, X., et al. B7-H3 and B7x are highly expressed in human prostate cancer and associated with disease spread and poor outcome. *Proc Natl Acad Sci USA* 104, 19458-19463 (2007).
3. Zang, X., et al. Tumor associated endothelial expression of B7-H3 predicts survival in ovarian carcinomas. *Mod Pathol*, May 21. [Epub ahead of print] (2010).
4. Sun, Y., et al. B7-H3 and B7-H4 expression in non-small-cell lung cancer. *Lung Cancer* 53, 143-151 (2006).
5. Tringler, B., et al. B7-H4 overexpression in ovarian tumors. *Gynecol Oncol* 100, 44-52 (2006).
6. Tringler, B., et al. B7-h4 is highly expressed in ductal and lobular breast cancer. *Clin Cancer Res* 11, 1842-1848 (2005).
7. Salceda, S., et al. The immunomodulatory protein B7-H4 is overexpressed in breast and ovarian cancers and promotes epithelial cell transformation. *Exp Cell Res* 306, 128-141 (2005).
8. Krambeck, A. E., et al. B7-H4 expression in renal cell carcinoma and tumor vasculature: associations with cancer progression and survival. *Proc Natl Acad Sci USA* 103, 10391-10396 (2006).
9. Yao, Y., et al. B7-H4 is preferentially expressed in non-dividing brain tumor cells and in a subset of brain tumor stem-like cells. *J Neurooncol* 89, 121-129 (2008).
10. Awadallah, N. S., et al. Detection of B7-H4 and p53 in pancreatic cancer: potential role as a cytological diagnostic adjunct. *Pancreas* 36, 200-206 (2008).
11. Tang, Q. & Bluestone, J. A. The Foxp3+ regulatory T cell: a jack of all trades, master of regulation. *Nat Immunol* 9, 239-244 (2008).
12. Littman, D. R. & Rudensky, A. Y. Th17 and regulatory T cells in mediating and restraining inflammation. *Cell* 140, 845-858 (2010).
13. Gabrilovich, D. I. & Nagaraj, S. Myeloid-derived suppressor cells as regulators of the immune system. *Nat Rev Immunol* 9, 162-174 (2009).
14. Marigo, I., Dolcetti, L., Serafini, P., Zanovello, P. & Bronte, V. Tumor-induced tolerance and immune suppression by myeloid derived suppressor cells. *Immunol Rev* 222, 162-179 (2008).
15. Abbas A K, Lichtman A H, Pober J S. Cellular and Molecular Immunology, 4$^{th}$ edition, W.B. Saunders Co., Philadelphia, 2000.
16. Allison et al. U.S. Patent Application Publication No. 2004/0157380, published Sep. 9, 2004, Compositions and methods for modulating lymphocyte activity.
17. Chen L J et al. B7-H4 expression associates with cancer progression and predicts patient's survival in human esophageal squamous cell carcinoma. Cancer Immunol Immunother 60(7):1047-55, 2011.
18. Quandt D et al. B7-h4 expression in human melanoma: its association with patients' survival and antitumor immune response. Clin Cancer Res. 17:3100-11, 2011.
19. Jiang J et al. Tumor expression of B7-H4 predicts poor survival of patients suffering from gastric cancer. Cancer Immunol Immunother. 59:1707-14, 2010.
20. Aslakson, C. J. & Miller, F. R. Selective events in the metastatic process defined by analysis of the sequential dissemination of subpopulations of a mouse mammary tumor. *Cancer Res* 52, 1399-1405 (1992).
21. Huang, A. Y., et al. The immunodominant major histocompatibility complex class I-restricted antigen of a murine colon tumor derives from an endogenous retroviral gene product. *Proc Natl Acad Sci USA* 93, 9730-9735 (1996).
22. Luznik, L., et al. Successful therapy of metastatic cancer using tumor vaccines in mixed allogeneic bone marrow chimeras. *Blood* 101, 1645-1652 (2003).
23. Fourcade, J., et al. Upregulation of Tim-3 and PD-1 expression is associated with tumor antigen-specific CD8+ T cell dysfunction in melanoma patients. *J Exp Med* 207, 2175-2186 (2010).
24. Zhou, Q., et al. Coexpression of Tim-3 and PD-1 identifies a CD8+ T-cell exhaustion phenotype in mice with disseminated acute myelogenous leukemia. *Blood* 117, 4501-4510 (2011).
25. Green, C. E., et al. Chemoattractant signaling between tumor cells and macrophages regulates cancer cell migration, metastasis and neovascularization. *PLoS One* 4, e6713 (2009).
26. Roda, J. M., et al. Stabilization of HIF-2alpha induces sVEGFR-1 production from tumor-associated macrophages and decreases tumor growth in a murine melanoma model. *J Immunol* 189, 3168-3177 (2012).
27. Roland, C. L., et al. Cytokine levels correlate with immune cell infiltration after anti-VEGF therapy in preclinical mouse models of breast cancer. *PLoS One* 4, e7669 (2009).
28. Tartour, E., et al. Angiogenesis and immunity: a bidirectional link potentially relevant for the monitoring of antiangiogenic therapy and the development of novel therapeutic combination with immunotherapy. *Cancer Metastasis Rev* 30, 83-95 (2011).
29. Chang, L. Y., et al. Tumor-derived chemokine CCL5 enhances TGF-beta-mediated killing of CD8(+) T cells in colon cancer by T-regulatory cells. *Cancer Res* 72, 1092-1102 (2012).
30. Fridlender, Z. G., et al. Polarization of tumor-associated neutrophil phenotype by TGF-beta: "N1" versus "N2" TAN. *Cancer Cell* 16, 183-194 (2009).
31. Clynes, R. A., Towers, T. L., Presta, L. G. & Ravetch, J. V. Inhibitory Fc receptors modulate in vivo cytotoxicity against tumor targets. *Nat Med* 6, 443-446 (2000).
32. Isitman, G., Stratov, I. & Kent, S. J. Antibody-Dependent Cellular Cytotoxicity and NK Cell-Driven Immune Escape in HIV Infection: Implications for HIV Vaccine Development. *Adv Virol* 2012, 637208 (2012).
33. Kohrt, H. E., et al. Combination strategies to enhance antitumor ADCC. *Immunotherapy* 4, 511-527 (2012).
34. Stover, C. Dual role of complement in tumour growth and metastasis (Review). *Int J Mot Med* 25, 307-313 (2010).
35. Zhu J. et al. B7-H4 Expression is Associated with Cancer Progression and Predicts Patient Survival in Human Thyroid Cancer. Asian Pac J Cancer Prev. 2013; 14(5):3011-5.
36. Liang M et al. T-cell infiltration and expressions of T lymphocyte co-inhibitory B7-H1 and B7-H4 molecules among colorectal cancer patients in northeast China's Heilongjiang province. Tumour Biol. 2013 Jul. 20. [Epub ahead of print].

What is claimed is:

1. An IgG1 monoclonal antibody or a fragment thereof comprising a means for selectively binding to human B7x amino acid residues 35-148 of SEQ ID NO: 1 with an equilibrium dissociation constant from residues 35-148 of SEQ ID NO: 1 that is less than 50 nM, wherein the IgG1 monoclonal antibody is capable of killing tumor cells through antibody-dependent cellular cytotoxicity.

2. The IgG1 monoclonal antibody or a fragment thereof of claim 1, wherein the IgG1 monoclonal antibody or fragment blocks inhibition of T cell function by binding to B7x.

3. The IgG1 monoclonal antibody or a fragment thereof of claim 1, wherein the IgG1 monoclonal antibody or fragment thereof does not include an antibody-partner molecule conjugate.

4. An IgG1 monoclonal antibody or a fragment thereof comprising a means for selectively binding to human B7x amino acid residues 35-148 of SEQ ID NO: 1 with an equilibrium dissociation constant from residues 35-148 of SEQ ID NO: 1 that is less than 50 nM, wherein the IgG1 monoclonal antibody is capable of preventing reoccurrence of a tumor by blocking inhibition of T cell function by B7x.

5. An IgG1 monoclonal antibody or a fragment thereof comprising a means for selectively binding to human B7x amino acid residues 35-148 of SEQ ID NO:1 with an equilibrium dissociation constant from residues 35-148 of SEQ ID NO: 1 that is less than 50 nM, wherein the IgG1 monoclonal antibody is capable of (i) treating a metastatic cancer or (ii) preventing metastasis of a cancer.

6. The IgG1 monoclonal antibody or a fragment thereof of claim 5, wherein a first level of B7x expression in a tumor sample from the metastatic cancer or the cancer is determined, and the first level of B7x expression in the tumor sample-is compared to a second level of B7x expression in a corresponding healthy tissue.

7. The IgG1 monoclonal antibody or a fragment thereof of claim 5, wherein the metastatic cancer or the cancer is a cancer of the skin, breast, pancreas, prostate, ovary, kidney, esophagus, gastrointestinal tract, colon, brain, liver, lung, head and/or neck.

8. A combination of anti-cancer agents comprising the IgG1 monoclonal antibody or a fragment thereof of claim 1, and a second anti-cancer agent that is not bound to the IgG1 monoclonal antibody or a fragment thereof.

9. The combination of claim 8, wherein the second anti-cancer agent is selected from the group consisting of an antibody against CTLA-4, an antibody against PD-1, an anti-EGFR agent, an alkylating agent, paclitaxel, docetaxel, and a topoisomerase inhibitor.

10. The combination of claim 9, wherein the second anti-cancer agent is an antibody against CTLA-4.

11. The combination of claim 9, wherein the anti-EGFR agent is selected from the group consisting of panitumumab, cetuximab, gefitinib and erlotinib.

12. The combination of claim 9, wherein the alkylating agent is selected from the group consisting of cisplatin, carboplatin, oxaliplatin, nedaplatin, satraplatin, triplatin tetranitrate, mechlorethamine, cyclophosphamide, chlorambucil and ifosfamide.

13. The combination of claim 9, wherein the topoisomerase inhibitor is selected from the group consisting of irinotecan, topotecan, amsacrine, etoposide, etoposide phosphate and teniposide.

* * * * *

SEQUENCE LISTING

<160> NUMBER OF SEQ ID NOS: 5

<210> SEQ ID NO 1
<211> LENGTH: 282
<212> TYPE: PRT
<213> ORGANISM: Homo sapiens

<400> SEQUENCE: 1

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280
```

<210> SEQ ID NO 2
<211> LENGTH: 283
<212> TYPE: PRT
<213> ORGANISM: Mouse

<400> SEQUENCE: 2

```
Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
```

```
              35                  40                  45
Gly Glu Asp Gly Thr Leu Ser Cys Thr Phe Glu Pro Asp Ile Lys Leu
 50                  55                  60

Asn Gly Ile Val Ile Gln Trp Leu Lys Glu Gly Ile Lys Gly Leu Val
 65                  70                  75                  80

His Glu Phe Lys Glu Gly Lys Asp Asp Leu Ser Gln Gln His Glu Met
                 85                  90                  95

Phe Arg Gly Arg Thr Ala Val Phe Ala Asp Gln Val Val Gly Asn
                100                 105                 110

Ala Ser Leu Arg Leu Lys Asn Val Gln Leu Thr Asp Ala Gly Thr Tyr
                115                 120                 125

Thr Cys Tyr Ile Arg Thr Ser Lys Gly Lys Gly Asn Ala Asn Leu Glu
130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
                180                 185                 190

Glu Val Ser Asn Thr Ser Phe Glu Leu Asn Ser Glu Asn Val Thr Met
                195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
                260                 265                 270

Leu Leu Ser Leu Ser Cys Cys Leu Met Leu Arg
                275                 280

<210> SEQ ID NO 3
<211> LENGTH: 849
<212> TYPE: DNA
<213> ORGANISM: Homo sapiens

<400> SEQUENCE: 3
atggcttccc tggggcagat cctcttctgg agcataatta gcatcatcat tattctggct      60
ggagcaattg cactcatcat tggctttggt atttcaggga cactccat cacagtcact       120 actgtcgcct cagctgggaa cattgggag atggaatcc tgagctgcac ttttgaacct      180
gacatcaaac tttctgatat cgtgatacaa tggctgaagg aagtgttttt aggcttggtc      240
catgagttca agaaggcaa agatgagctg tcggagcagg atgaaatgtt cagaggccgg      300
acagcagtgt ttgctgatca agtgatagtt ggcaatgcct ctttgcggct gaaaaacgtg      360
caactcacag atgctggcac ctacaaatgt tatatcatca cttctaaagg caaggggaat      420
gctaaccttg agtataaaac tggagccttc agcatgccgg aagtgaatgt ggactataat      480
gccagctcag agaccttgcg gtgtgaggct ccccgatggt tccccagcc acagtggtc      540 tgggcatccc aagttgacca gggagccaac ttctcggaag tctccaatac cagctttgag      600
ctgaactctg agaatgtgac catgaaggtt gtgtctgtgc tctacaatgt tacgatcaac      660
aacacatact cctgtatgat tgaaaatgac attgccaaag caacagggga tatcaaagtg      720
```

```
acagaatcgg agatcaaaag gcggagtcac ctacagctgc taaactcaaa ggcttctctg      780
tgtgtctctt ctttctttgc catcagctgg gcacttctgc ctctcagccc ttacctgatg      840
ctaaaataa                                                               849

<210> SEQ ID NO 4
<211> LENGTH: 852
<212> TYPE: DNA
<213> ORGANISM: Mouse

<400> SEQUENCE: 4
atggcttcct tggggcagat catcttttgg agtattatta acatcatcat catcctggct       60
ggggccatcg cactcatcat tggctttggc atttcaggca agcacttcat cacggtcacg      120
accttcacct cagctggaaa cattggagag gacgggaccc tgagctgcac ttttgaacct      180
gacatcaaac tcaacggcat cgtcatccag tggctgaaag aaggcatcaa aggtttggtc      240
cacgagttca agaaggcaa agacgacctc tcacagcagc atgagatgtt cagaggccgc       300
acagcagtgt ttgctgatca ggtggtagtt ggcaatgctt ccctgagact gaaaaacgtg      360
cagctcacgg atgctggcac ctacacatgt tacatccgca cctcaaaagg caagggaat       420 gcaaacctag agtataagac cggagccttc agtatgccag agataaatgt ggactataat      480
gccagttcag agagtttacg ctgcgaggct cctcggtggt tcccccagcc cacagtggcc      540
tgggcatctc aagtcgacca aggagccaac ttctcagaag tctcgaacac cagctttgag      600
ttgaactctg agaatgtgac catgaaggtc gtatctgtgc tctacaatgt cacaatcaac      660
aacacatact cctgtatgat tgaaaatgac attgccaaag ccactgggga catcaaagtg      720
acagattcag aggtcaaaag gcggagtcag ctgcagctgc tcaactccgg gccttccccg      780
tgtgtttttt cttctgcctt tgcggctggc tgggcgctcc tatctctctc ctgttgcctg      840
atgctaagat ga                                                          852

<210> SEQ ID NO 5
<211> LENGTH: 9
<212> TYPE: PRT
<213> ORGANISM: Artificial Sequence
<220> FEATURE:
<223> OTHER INFORMATION: tumor antigen
<220> FEATURE:
<221> NAME/KEY: MISC_FEATURE
<222> LOCATION: (9)..(9)
<223> OTHER INFORMATION: x = F or H

<400> SEQUENCE: 5

Ser Pro Ser Tyr Val Tyr His Gln Xaa
1               5
```